(12) United States Patent
Kahl

(10) Patent No.: US 11,779,283 B2
(45) Date of Patent: Oct. 10, 2023

(54) PROCESS AND SIGNAL PROCESSING UNIT FOR DETERMINING A CARDIOGENIC SIGNAL

(71) Applicant: Drägerwerk AG & Co. KGaA, Lübeck (DE)

(72) Inventor: Lorenz Kahl, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 183 days.

(21) Appl. No.: 17/242,663

(22) Filed: Apr. 28, 2021

(65) Prior Publication Data

US 2021/0338176 A1 Nov. 4, 2021

(30) Foreign Application Priority Data

Apr. 29, 2020 (DE) ..................... 10 2020 002 572.2

(51) Int. Cl.
*A61B 5/00* (2006.01)
*A61B 5/0205* (2006.01)
(Continued)

(52) U.S. Cl.
CPC .......... *A61B 5/7278* (2013.01); *A61B 5/0205* (2013.01); *A61B 5/7203* (2013.01);
(Continued)

(58) Field of Classification Search
CPC ... A61B 5/7278; A61B 5/7203; A61B 5/0816; A61B 5/0205; A61B 5/7289; A61B 5/08;
(Continued)

(56) References Cited

U.S. PATENT DOCUMENTS

| 8,109,269 | B2 | 2/2012 | Eger | |
|---|---|---|---|---|
| 2016/0199606 | A1* | 7/2016 | Eger | .................. A61M 16/026 128/204.23 |
| 2022/0330837 | A1 | 10/2022 | Kahl et al. | |

FOREIGN PATENT DOCUMENTS

| DE | 102007062214 B3 | 8/2009 |
|---|---|---|
| DE | 102011016804 A1 | 10/2012 |

(Continued)

OTHER PUBLICATIONS

Strobach P, Abraham-Fuchs K, Härer W. Event-synchronous cancellation of the heart interference in biomedical signals. IEEE Trans Biomed Eng. Apr. 1994;41(4):343-50. doi: 10.1109/10.284962. PMID: 8063300 (Year: 1994).*

(Continued)

*Primary Examiner* — Eric F Winakur
*Assistant Examiner* — Elina Sohyun Ahn
(74) *Attorney, Agent, or Firm* — McGlew and Tuttle, P.C.

(57) ABSTRACT

A process and unit for determining an estimate for a respiratory signal. Measured values are received, and a sum signal is generated, which is a superimposition of the respiratory signal to a cardiogenic signal. The unit detects heartbeats, and a respective heartbeat time period for each. An intermediate signal is calculated by compensating the influence of the cardiac activity on the sum signal. The unit determines an attenuation signal, which is an indicator of the average time curve of the contribution of the cardiogenic signal to the intermediate signal in a predefined reference heartbeat time period. An intermediate signal section is generated as a section of the intermediate signal in a heartbeat time period and intermediate signal sections are mapped to the reference heartbeat time period. The estimated respiratory signal is calculated with the use of the mapped intermediate signal sections and of the attenuation signal.

17 Claims, 21 Drawing Sheets

(51) Int. Cl.
  *G06N 20/00* (2019.01)
  *G16H 40/63* (2018.01)
  *A61M 16/00* (2006.01)
  *A61B 5/0255* (2006.01)
  *A61B 5/08* (2006.01)

(52) U.S. Cl.
  CPC .......... *A61B 5/7246* (2013.01); *A61B 5/7289* (2013.01); *G06N 20/00* (2019.01); *G16H 40/63* (2018.01); *A61B 5/0255* (2013.01); *A61B 5/0816* (2013.01); *A61M 16/0003* (2014.02)

(58) Field of Classification Search
  CPC .. A61M 16/0069; A61M 16/024; G16H 40/63
  See application file for complete search history.

(56) References Cited

FOREIGN PATENT DOCUMENTS

| DE | 102015015296 A1 | 6/2017 |
|---|---|---|
| DE | 102019006866 A1 | 4/2021 |
| EP | 2845616 A1 | 3/2015 |
| EP | 3381354 A1 | 10/2018 |
| EP | 2845616 B1 | 1/2019 |
| GB | 2455844 A | 6/2009 |

OTHER PUBLICATIONS

M. Ungureanu and W. M. Wolf: "Basic Aspects Concerning the Event-Synchronous Interference Canceller," IEEE Transactions on Biomedical Engineering, vol. 53, No. 11 (2006), pp. 2240-2247.

L. Kahl and U. G. Hofmann: "Removal of ECG artifacts from EMG signals with different artifact magnitudes by template subtraction," Current Directions in Biomedical Engineering, 2019; 5(1), pp. 357-360.

S. Abbaspour and A. Fallah: "A Combination Method for Electrocardiogram Rejection from Surface Electromyogram," Open Biomedical Engineering Journal, vol. 8 (2014), pp. 13-19.

Alher Mauricio Hernández Valdivieso: "Assessment of weaning indexes based on diaphragm activity in mechanically ventilated subjects after cardiovascular surgery., A pilot study", Rev Bras Ter Intensiva, Feb. 20, 2017, 213-221, 29(2).

Rtega, Isabel, et al. Assessment of Weaning Indexes Based on Diaphragm Activity in Mechanically Ventilated ubjects after Cardiovascular Surgery. A Pilot Study. Bioinstrumentation and Clinical Engineering Research Group, ioengineering Program. Medellin, Colombia.

* cited by examiner

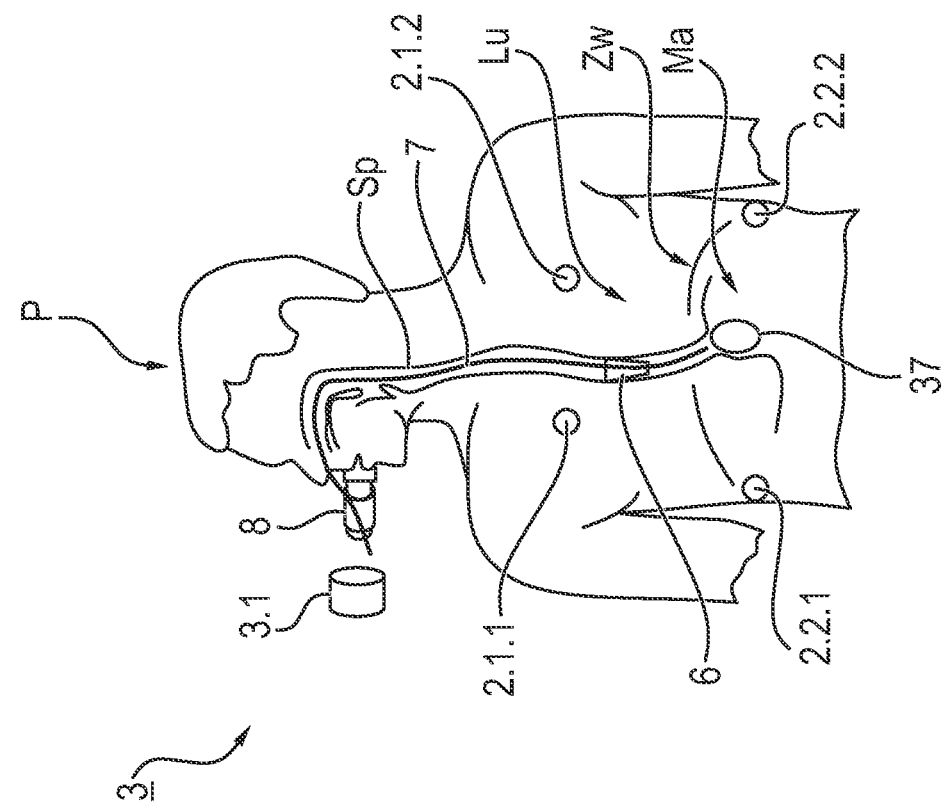
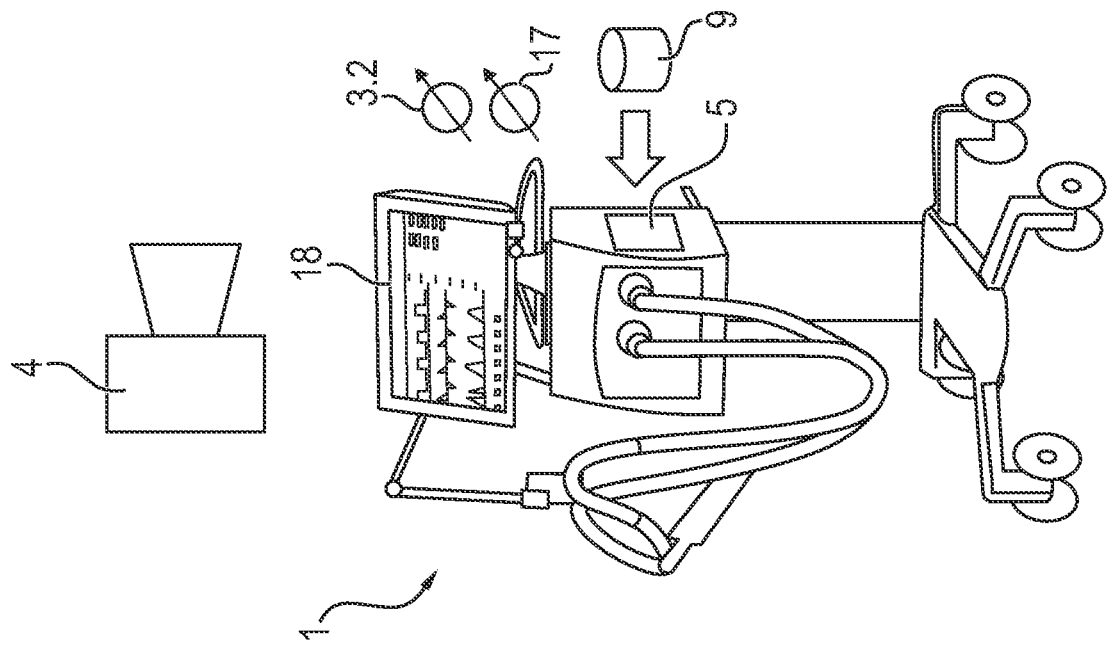
FIG. 1

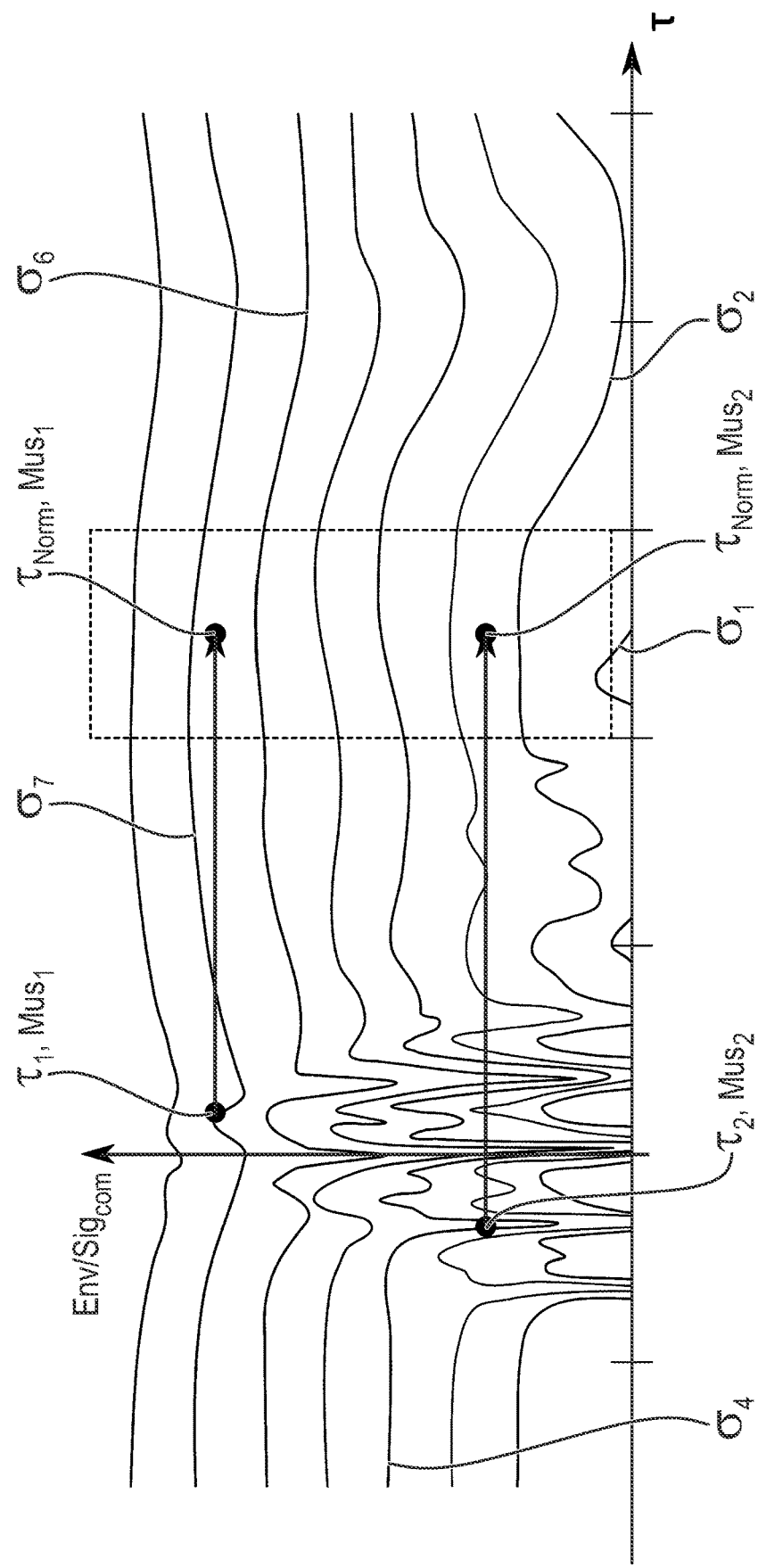

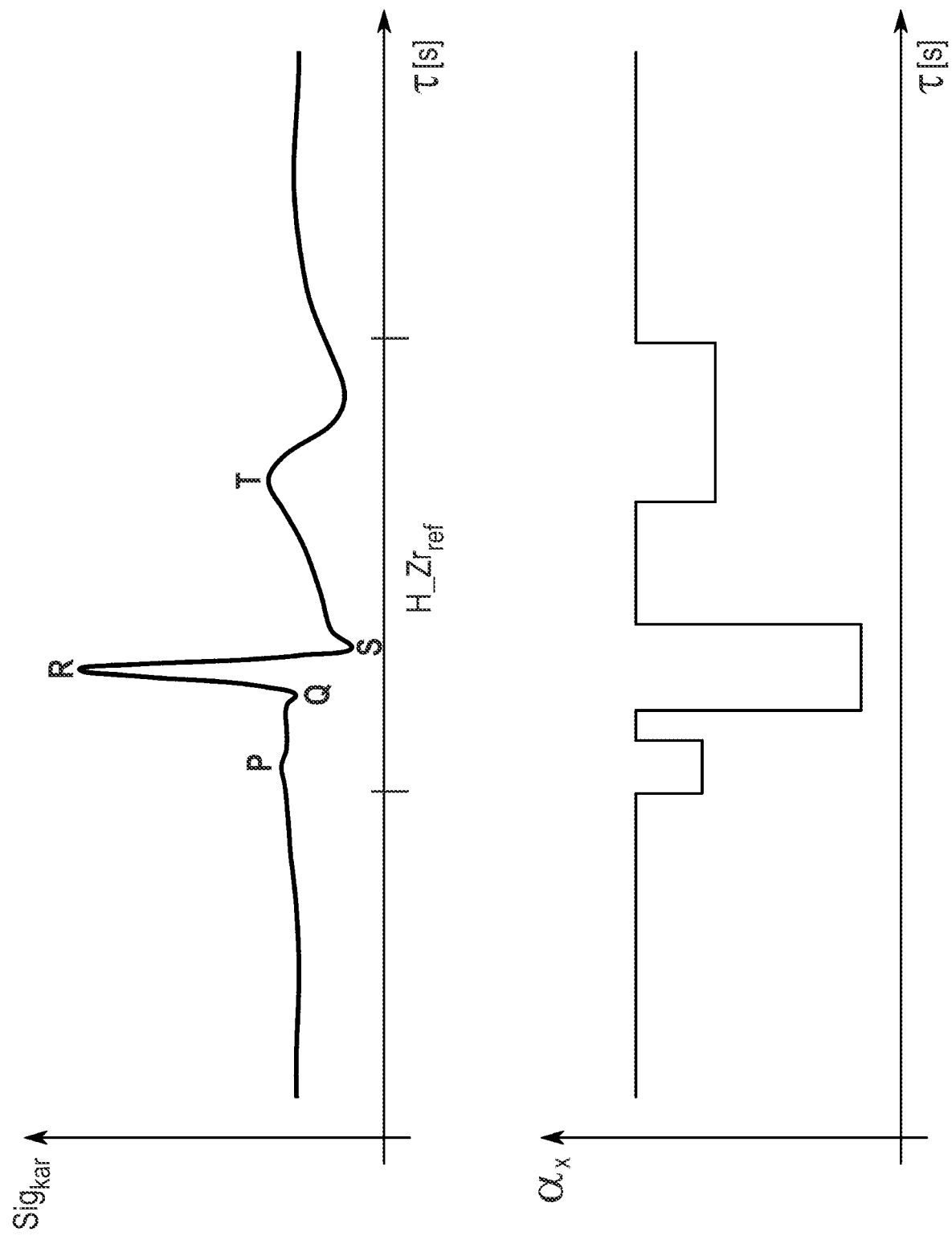

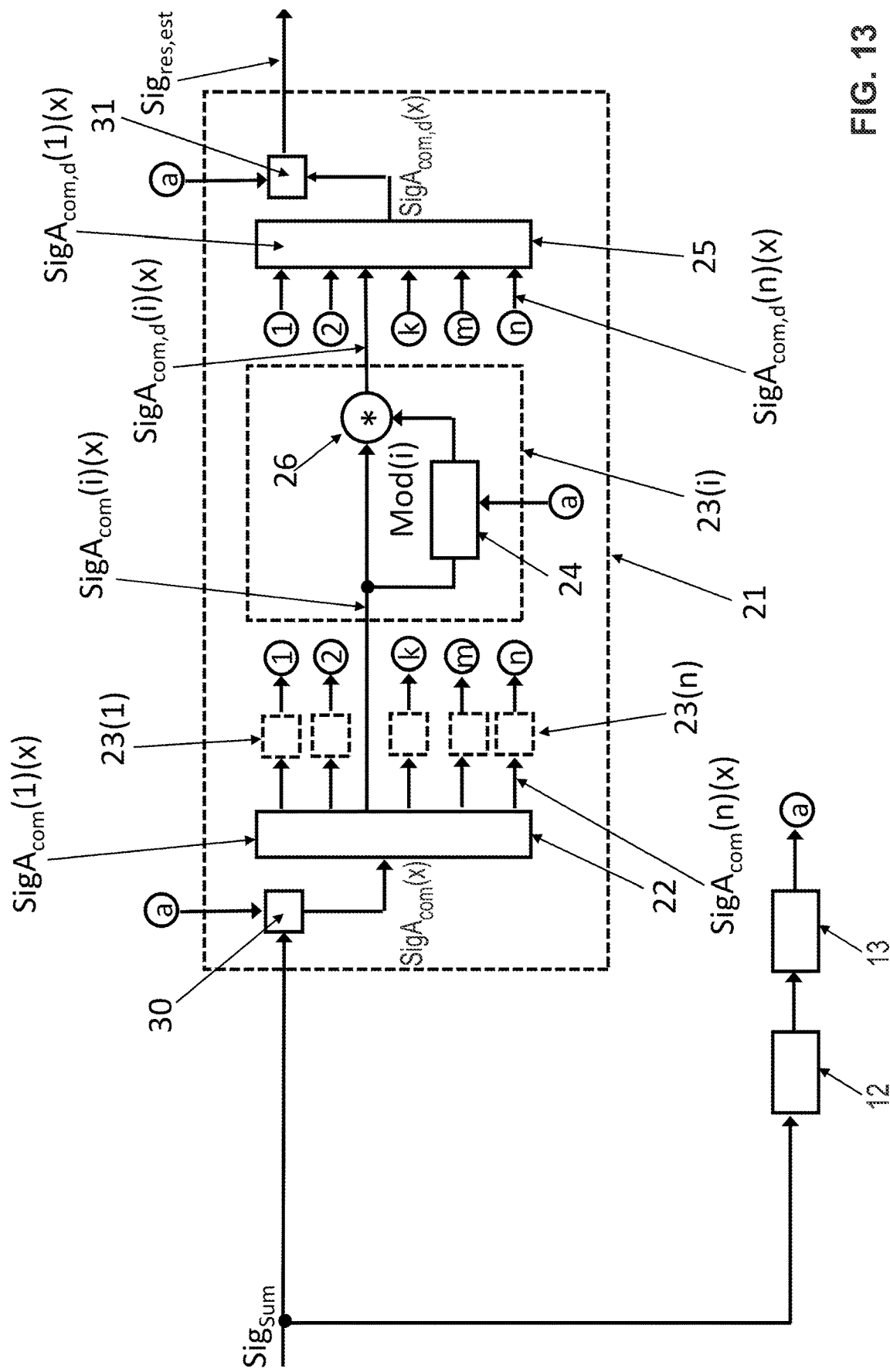

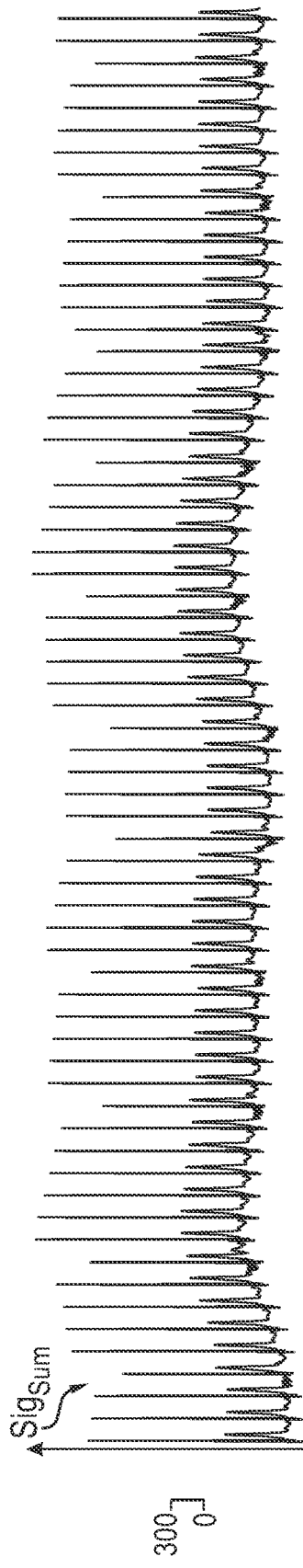
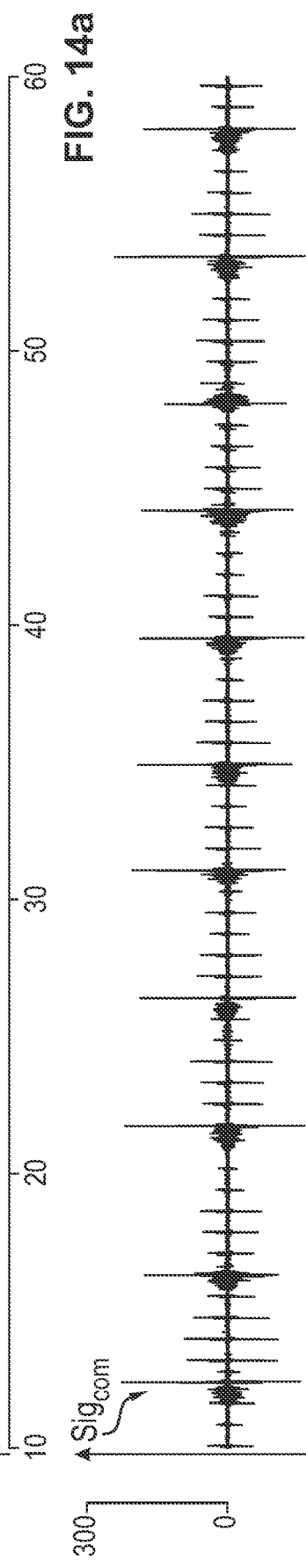
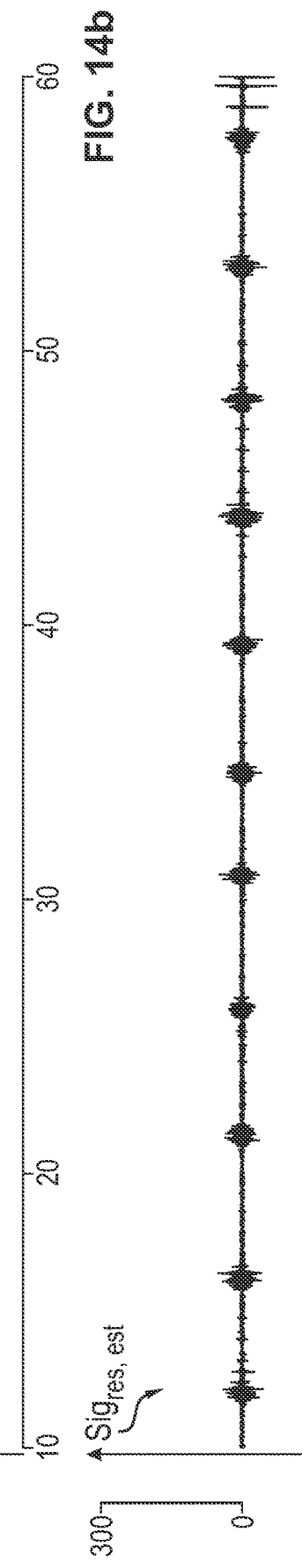
FIG. 14a
FIG. 14b
FIG. 14c

PROCESS AND SIGNAL PROCESSING UNIT FOR DETERMINING A CARDIOGENIC SIGNAL

CROSS REFERENCE TO RELATED APPLICATIONS

This application claims the benefit of priority under 35 U.S.C. § 119 of German Application 10 2020 002 572.2, filed Apr. 29, 2020, the entire contents of which are incorporated herein by reference.

TECHNICAL FIELD

The present invention pertains to a process and to a signal processing unit, which automatically determine an estimate for a respiratory signal. This respiratory signal to be determined is an indicator of an intrinsic breathing activity and/or of the mechanical ventilation of a patient. The intrinsic breathing activity is performed by the respiratory muscles of the patient and comprises the spontaneous breathing as well as a breathing stimulated from the outside by means of the respiratory muscles. The respiratory signal is needed, for example, or can be used to determine the status of the respiratory muscles of the patient and/or to adapt the mechanical ventilation to the spontaneous breathing of the patient, especially in order to regulate the ventilator, which is used for the mechanical ventilation

TECHNICAL BACKGROUND

The respiratory signal cannot, as a rule, be measured directly. It is rather only possible to measure a signal, which results from a superimposition of the respiratory signal being sought and a cardiogenic signal and optionally unwanted signals. The cardiogenic signal is an indicator of the cardiac activity of the patient. This signal formed from a superimposition will hereinafter be called "sum signal."

SUMMARY

A basic object of the present invention is to provide a process and a signal processing unit, which are capable of removing the cardiogenic signal component from a sum signal by calculation better than prior-art processes, wherein the sum signal has been generated from measured values that have been measured at a patient and comprises a superimposition of the respiratory signal and a cardiogenic signal.

The object is accomplished by a process wherein a reference heartbeat time period is predefined for the process, wherein the process is carried out automatically with the use of a data-processing signal processing unit, wherein the sum signal comprises a superimposition, wherein the signal processing unit receives measured values of at least one sum signal sensor, which measures a signal generated in the body of the patient, generates a sum signal with the use of such measured values, wherein the sum signal comprises a superimposition of the respiratory signal to be estimated and of a cardiogenic signal, which is correlated with the cardiac activity of the patient. The signal processing unit detects a plurality of heartbeats and a respective heartbeat time period, in which said heartbeat takes place, for each detected heartbeat, with the use of the sum signal, and calculates from the sum signal an intermediate signal, wherein it compensates the influence of the cardiac activity on the sum signal by calculation at least approximately, or uses the sum signal as the intermediate signal. The signal processing unit calculates at least one attenuation signal or determines this attenuation signal by a read access to a memory. The attenuation signal or each attenuation signal with the average time curve of the contribution of the cardiogenic signal is correlated with the intermediate signal in the reference heartbeat time period. The signal processing unit generates for at least one detected heartbeat, preferably for each detected heartbeat a respective intermediate signal section as a section of the intermediate signal, which is located in the heartbeat time period of this heartbeat, determines for at least one and preferably for each scanning time in the heartbeat time period of this heartbeat the reference time in the reference heartbeat time period, which corresponds to this scanning time, and determines the respective value of the attenuation signal or each attenuation signal at this reference time, and generates an attenuated intermediate signal section for the heartbeat time period from the intermediate signal section with the use of the attenuation signal values thus determined. The attenuated intermediate signal section is correlated with the curve of the respiratory signal in the heartbeat time period. The signal processing unit generates the estimate for the respiratory signal with the use of the attenuated intermediate signal section or each attenuated intermediate signal section.

The object is accomplished by a signal processing unit which has read access at least at times to a memory and preferably write access at least at times to the memory and is configured to automatically determine an estimate for a respiratory signal. The respiratory signal is correlated with the intrinsic breathing activity and the mechanical ventilation of a patient. A computer-accessible description of a reference heartbeat time period is stored in the memory. The signal processing unit is configured to receive measured values from at least one sum signal sensor. The sum signal sensor or each sum signal sensor is configured to measure a signal generated in the body of the patient. The signal processing unit is configured to generate a sum signal with the use of such measured values. The sum signal comprises a superimposition of the respiratory signal to be estimated and of a cardiogenic signal, which is correlated with the cardiac activity of the patient. The signal processing unit is configured to detect a plurality of heartbeats and a respective heartbeat time period in which this heartbeat takes place for each detected heartbeat. The signal processing unit is configured to calculate an intermediate signal by an approximate compensation by calculation of the influence of the cardiac activity on the sum signal, or to use the sum signal as the intermediate signal. The signal processing unit is configured to calculate at least one attenuation signal or to determine this by a read access to the memory. The attenuation signal or each attenuation signal is correlated with the average time curve of the contribution of the cardiogenic signal to the intermediate signal in the reference heartbeat time period. The signal processing unit is configured to generate for at least one detected heartbeat, preferably for each detected heartbeat, an intermediate signal section as a section of the intermediate signal, which is in the heartbeat time period of this heartbeat. The signal processing unit is configured to determine, for at least one and preferably for each scanning time in the heartbeat time period of this heartbeat, the reference time in the reference heartbeat time period, which corresponds to this scanning time (t), and to determine the respective value of the attenuation signal or each attenuation signal at this reference time. The signal processing unit is configured to generate an attenuated intermediate signal section for the heartbeat time period from the intermediate signal section with the use of the attenuation signal values thus determined. The attenuated intermediate signal section is correlated with the curve of the respiratory signal in the heartbeat time period. The signal processing unit is configured to generate the estimate for the respiratory signal with the use of the attenuated intermediate signal section or each attenuated intermediate signal.

Advantageous embodiments of the process according to the present invention are also corresponding advantageous embodiments of the signal processing unit according to the present invention and vice versa, where meaningful.

An estimate is determined for a respiratory signal by the process according to the present invention and by the signal processing unit according to the present invention. The respiratory signal and hence also the estimate determined are correlated with the intrinsic breathing activity and/or with the mechanical ventilation of a patient. It is possible that the patient is ventilated mechanically and the mechanical ventilation is superimposed to the intrinsic breathing activity of the patient. The respiratory signal is correlated in this case with this superimposition. It is also possible that the patient is fully sedated and is not performing any intrinsic breathing activity.

The signal processing unit according to the present invention is configured to carry out the process according to the present invention automatically, and has read access to a memory at least from time to time. The signal processing unit preferably also has write access to this memory at least from time to time. The process according to the present invention is carried out automatically. A computer-accessible specification of a reference heartbeat time period is predefined for the process. A computer-accessible specification of this reference heartbeat time period is stored in the memory.

A cardiogenic signal, which is correlated with the heartbeat of a person, shows a typical progress over time. It is only in the course of a heartbeat that this signal assumes values that deviate from zero more greatly than a threshold. A heartbeat time period is a period during which these signal values deviate in their value from zero more greatly than a threshold. A reference heartbeat time period is a reference time period that covers a typical heartbeat time period. Each time period of a heartbeat time period corresponds to a reference time in the reference heartbeat time period. In case of an electrical cardiogenic signal, this reference heartbeat time period covers in an adolescent or adult, for example, a time period of −0.25 sec to +0.65 sec or −0.15 sec to +0.6 sec, and a shorter time period in a child, and a characteristic heartbeat time, e.g., the so-called R wave, is at 0 sec. It is possible that two consecutive heartbeat time periods follow one another directly. A time gap may occur between consecutive heartbeat time periods.

The signal processing unit receives measured values from at least one sum signal sensor, preferably from a plurality of sum signal sensors. The sum signal sensor or each sum signal sensor measures a signal generated in the body of the patient. A sum signal sensor may be arranged in or at the body of the patient or it may also measure a signal generated in the body of the patient in a contactless manner or from a distance. This signal is especially an electrical or mechanical or pneumatic or optical or plethysmographic signal (correlated with the current volume of blood in a blood vessel), especially a signal generated by optical plethysmography (photoplethysmography) or a signal derived from this.

The signal processing unit generates a sum signal. This sum signal results from a superimposition of the respiratory signal to be estimated, a cardiogenic signal as well as optionally additionally unwanted signals, especially additional signals generated in the body of the patient. The cardiogenic signal is correlated with the cardiac activity of the patient. The signal processing unit generates the sum signal with the use of measured values of the sum signal sensor or of at least one sum signal sensor, optionally of measured values of a plurality of sum signal sensors.

The signal processing unit detects a plurality of heartbeats of the patient. The signal processing unit detects for each detected heartbeat a respective heartbeat time period, during which this heartbeat takes place. The signal processing unit uses the generated sum signal for this detection.

The sum signal results from a superimposition of the respiratory activity and the heartbeat activity of the patient. The signal processing unit calculates from the sum signal an intermediate signal. During this calculation, the signal processing unit approximately compensates by calculation the influence of the cardiac activity of the patient on the sum signal, and the compensation yields the intermediate signal. In an alternative embodiment, the signal processing unit uses the sum signal directly as the intermediate signal.

The signal processing unit determines at least one attenuation signal, and optionally a plurality of attenuation signals. In one embodiment, the signal processing unit calculates the attenuation signal, preferably on the basis of a random sample with signals that were measured at the patient. In another embodiment, it determines the attenuation signal by a read access to the memory, in which the attenuation signal is stored, preferably an average attenuation signal, which is valid for a plurality of heartbeats or for all heartbeats. The attenuation signal or each attenuation signal is an indicator of the average time curve of the contribution that the cardiogenic signal has in the predefined reference heartbeat time period made to the intermediate signal, i.e., it is correlated with this contribution. This contribution and hence the attenuation signal or each attenuation signal vary in the course of the reference heartbeat time period, which is why the term "time curve of the contribution" was coined.

The signal processing unit generates for at least one detected heartbeat an intermediate signal section. It preferably generates a respective intermediate signal section for each detected heartbeat. The intermediate signal section is the section of the intermediate signal that is in the heartbeat time period of this detected heartbeat.

The signal processing unit carries out the determination of the estimated respiratory signal for a plurality of consecutive scanning times. Exactly one reference time corresponds to each scanning time in the predefined reference heartbeat time period, unless the scanning time is outside a heartbeat time period. Different scanning times may correspond to the same reference time. The signal processing unit determines for at least one scanning time the reference time that corresponds to this scanning time. It preferably determines the corresponding reference time in the reference heartbeat time period for each scanning time.

The signal processing unit determines the respective value that the attenuation signal or each attenuation signal assumes at this reference time.

The signal processing unit generates an attenuated intermediate signal section for the heartbeat time period from each intermediate signal section. Each signal value of the attenuated intermediate signal section has a lower value than or the same value as the signal value of the intermediate signal section for the same reference time. To calculate the attenuated intermediate signal section, the signal processing unit uses the intermediate signal section and the determined values of the attenuation signal or of at least one attenuation signal. This attenuated intermediate signal section is correlated with the course of the respiratory signal in the heartbeat time period.

To generate the sought estimate for the respiratory signal, the signal processing unit uses the attenuated intermediate signal section or each attenuation signal section. For example, it assembles the attenuated intermediate signal sections into the sought respiratory signal. When needed, the signal processing unit automatically fills in gaps between two consecutive attenuated intermediate signal sections in a suitable manner.

The present invention shows a way for determining an estimate for the respiratory signal from the sum signal. The knowledge of the respiratory signal can be used, for example, to regulate or to control a ventilator and to adapt in the process especially the ventilation strokes, which the ventilator carries out, to the intrinsic breathing activity of the patient. It is not possible in many cases to measure this respiratory signal directly because the cardiogenic signal and optional unwanted signals are superimposed to the respiratory signal at each scanning time.

A two-step process is carried out according to the present invention in order to determine the respiratory signal. The intermediate signal is generated in the first step by approximately compensating the influence of the cardiogenic signal on the sum signal by calculation. It is not possible, as a rule, to fully compensate the influence of the cardiogenic signal by this compensation by calculation. The second step is carried out therefore. It is also possible to carry out only the second step.

The second step is based on the discovery that at least in the section of a heartbeat time period, and optionally in the entire heartbeat time period, the influence of the cardiogenic signal on the sum signal is considerably greater than the influence of the respiratory signal. By contrast, the sum signal is determined predominantly or even exclusively by the respiratory signal between two consecutive heartbeat time periods. The attenuation signal compensates at least approximately the influence of the cardiogenic signal on the intermediate signal, especially the influence/contribution that remains after the compensation in the first step.

It is possible that a time period that is free from a cardiac activity of the patient occurs between two detected heartbeat time periods following one another directly. The signal processing unit preferably calculates a non-attenuated intermediate signal section for this intermediate period. It uses for this the intermediate signal. In one embodiment, the signal processing unit uses the signal section of the intermediate signal that is related to this heartbeat-free time period as the non-attenuated intermediate signal section.

The signal processing unit assembles the attenuated intermediate signal sections into the sought estimate of the respiratory signal. If present, it inserts a non-attenuated intermediate signal section each between two attenuated intermediate signal sections for two consecutive heartbeat time periods.

In one embodiment, the attenuation signal or each attenuation signal is predefined and stored in advance in the memory. In a preferred embodiment, the signal processing unit calculates, by contrast, automatically the attenuation signal or at least one attenuation signal and stores the attenuation signal or each calculated attenuation signal in the memory. The operation of calculating the attenuation signal or an attenuation signal preferably comprises the following steps:

The signal processing unit generates a random sample with signal sections. This signal section random sample comprises the respective intermediate signal section, which pertains to this heartbeat and is correlated with the curve of the respiratory signal in this heartbeat time period, for a plurality of detected heartbeats.

The signal processing unit maps each intermediate signal section of the signal section random sample by calculation to the predefined reference heartbeat time period. It preferably maps in this connection at least one and preferably each scanning time of the intermediate signal section to the corresponding reference time of the reference heartbeat time period. Due to this mapping being carried out for each intermediate time section of the signal section random sample, the images of the intermediate signal sections are superimposed by calculation in the reference heartbeat time period.

The signal processing unit calculates the attenuation signal, for which it uses the mapped intermediate signal sections of the signal section random sample and preferably generates a statistical mean value.

This embodiment makes it possible to automatically adapt the attenuation signal to the patient and to the current state of the patient. It is not necessary to predefine the same attenuation signal permanently, to store it in the memory and to use it repeatedly for each patient. It is made rather possible to determine the signal section random sample and to calculate the attenuation signal, which can be adapted to the patient, as a function of the signal section random sample, as was just described. This initialization phase can be carried out anew for each mechanical ventilation of a patient. It is also possible that the signal processing unit updates the attenuation signal for a patient continuously.

According to this embodiment, the intermediate signal sections are superimposed by calculation to the signal section random sample in the reference heartbeat time period, and a suitable statistical process is then applied. The influence of the respiratory signal on the intermediate signal sections is largely eliminated in many applications by averaging, and the attenuation signal depends only on the remaining contribution of the cardiogenic signal to the intermediate signal. In many cases, the attenuation signal is a good indicator of the cardiogenic signal in the reference heartbeat time period.

In a variant of this embodiment, the step of calculating the attenuation signal comprises the following steps:

The signal processing unit calculates a random sample for a predefined performance or power indicator. This random sample comprises a plurality of time curves of an indicator, which is correlated with an electrical or mechanical or pneumatic or plethysmographic performance or a performance measured in another manner in the reference heartbeat time period.

In the step in which the random sample is calculated, the signal processing unit calculates for a plurality of intermediate signal sections of the signal section random sample a respective time curve of the performance/power indicator in the reference heartbeat time period. The signal processing unit preferably carries out this calculation for each intermediate signal section of the signal section random sample.

The signal processing unit calculates an average time curve of the performance indicator in the reference heartbeat time period. The signal processing unit carries out here a suitable statistical averaging over the time curves for the intermediate signal sections.

The signal processing unit calculates the attenuation signal with the use of the average time curve of the performance indicator. In particular, it uses a statistical averaging over the time curves as the attenuation signal.

This embodiment uses the fact that the cardiogenic signal makes a substantial contribution to the intermediate signal section for this heartbeat time period during a heartbeat time period. The performance indicator therefore depends substantially on the contribution of the cardiogenic signal. The contribution of the respiratory signal is, by contrast, largely "eliminated by calculation" by the averaging over the random sample.

The higher the value of the average time curve of the performance indicator of a given reference time, the lower is preferably the value of the attenuation signal for a reference time.

In one embodiment, the signal processing unit calculates a performance average, which indicates the average electrical or mechanical or pneumatic or plethysmographic performance in the course of the reference heartbeat time period. The signal processing unit uses for this calculation the performance indicator random sample. To calculate the attenuation signal, the signal processing unit uses the average time curve of the performance indicator as well as additionally the performance average. In one embodiment, the signal processing unit calculates the attenuation signal with the use of the quotient of the performance average and the average time curve of the performance indicator and uses, for example, this quotient as the attenuation signal.

In one embodiment of how the attenuation signal is calculated, the standard reference time of the reference heartbeat time period is predefined. The cardiogenic signal is negligibly small at this standard reference time compared to the respiratory signal.

The signal processing unit additionally carries out the following steps according to this embodiment:

For at least one reference time of the reference heartbeat time period, the signal processing unit generates a signal value random sample, and optionally a respective signal value random sample each for a plurality of reference times. The signal value random sample or each signal value random sample comprises the values at this reference time of the intermediate signal sections of the signal section random sample, which said intermediate signal sections are mapped to the reference heartbeat time period.

The signal processing unit calculates an empirical distribution function for the reference time or for each reference time. It uses the signal value random sample for this reference time for this purpose.

The signal processing unit generates a standard signal value random sample. This standard signal value random sample comprises the values at the standard reference time of the mapped intermediate signal sections of the signal section random sample.

The signal processing unit calculates an empirical standard distribution function for the standard reference time. It uses the standard signal value random sample for this purpose.

The signal processing unit calculates the attenuation signal, for which it uses the empirical distribution function or each empirical distribution function as well as the empirical standard distribution function.

The standard signal value random sample indicates an average curve at a standard reference time, at which the cardiac activity (heartbeat activity) and therefore the cardiogenic signal have practically no effect. The signal value random sample indicates an average curve at a reference time, at which the cardiac activity can have an effect.

In one embodiment, a plurality of frequency bands are predefined, and these frequency bands preferably cover together the entire frequency spectrum of the human heartbeat and of the human breathing and optionally of a mechanical ventilation—more precisely: The entire possible frequency spectrum of a sum signal generated according to the present invention, which results from a superimposition of the respiratory signal to the cardiogenic signal. The steps according to the present invention, which were just described, are carried out for each frequency band. The following steps are carried out according to this embodiment:

The signal processing unit calculates for each predefined frequency band at least one respective attenuation signal. This attenuation signal is an indicator of the contribution of the component of the cardiogenic signal that is in this frequency band to the intermediate signal—more precisely, an indicator of the time curve of this contribution in the predefined reference heartbeat time period.

The signal processing unit calculates for at least one detected heartbeat and for each predefined frequency band a respective component of the intermediate signal section for the heartbeat time period of this detected heartbeat, namely, the component of the intermediate signal section occurring in this frequency band. The signal processing unit preferably calculates this component for each frequency band and for each detected heartbeat.

The signal processing unit generates an attenuated intermediate signal section component, which is related to this frequency band and to this heartbeat, for each predefined frequency band. This step is preferably carried out for each detected heartbeat and for each predefined frequency band. The signal processing unit uses for the generation the component of the intermediate signal section that occurs in this frequency band.

The signal processing unit generates the attenuated intermediate signal section for a detected heartbeat, for which it uses the attenuated intermediate signal section components of the frequency bands, which components are generated for this heartbeat.

This embodiment makes it possible to compensate the cardiogenic component of the sum signal separately for each frequency band. This leads in some cases to better results than if an averaged compensation were carried out over all frequencies.

According to the present invention, the signal processing unit calculates from the sum signal an intermediate signal, and the signal processing unit compensates the influence of the cardiogenic signal at least partially. In one embodiment, the signal processing unit uses a cardiogenic reference signal section to calculate the intermediate signal. This cardiogenic reference signal section describes an average time curve of the cardiogenic signal in the curve of the reference heartbeat time period, i.e., it is a template for the cardiogenic signal.

In one embodiment, this cardiogenic reference signal section is predefined in advance and is stored in the memory. In a preferred embodiment, the step of calculating the intermediate signal comprises, by contrast, the following steps:

The signal processing unit generates a cardiogenic reference signal section and stores it in the memory. The signal processing unit uses a plurality of detected heartbeat time periods as well as the sum signal to generate the cardiogenic reference signal section.

The signal processing unit preferably generates for each heartbeat time period a respective sum signal section, which describes the course of the sum signal in this heartbeat time period, and it maps this sum signal section to the reference heartbeat time period. Due to this being carried out for a plurality of sum signal sections, the sum signal sections are superimposed by calculation. The signal processing unit uses a statistical method, for example, an averaging, to calculate the cardiogenic reference signal section from the sum signal sections superimposed by calculation.

The signal processing unit calculates a compensated signal as the intermediate signal. The signal processing unit compensates here the influence of the cardiac activity on the sum signal during a detected heartbeat by calculation. The signal processing unit uses for this calculation-based compensation the detected heartbeat time period of this heartbeat as well as the cardiogenic reference signal section, which was generated and stored in the memory before.

This embodiment makes it possible to adapt the cardiogenic reference signal section to the patient and his current state.

In a variant of this embodiment, the signal processing unit uses the same cardiogenic reference signal section for each heartbeat. In another variant of this embodiment, the signal processing unit measures for at least one heartbeat a detected heartbeat, especially preferably at least one respective value, which a predefined anthropological parameter assumes at this heartbeat, for each detected heartbeat. The parameter is, for example, the filling level of the lungs or an indicator of the current posture of the patient. The signal processing unit calculates an adapted signal section for the heartbeat time period. The signal processing unit uses for this the cardiogenic reference signal section, which is stored in the memory, as well as the value or at least one value of the anthropological parameter or of an anthropological parameter, which was measured during this heartbeat.

This embodiment with the value of the anthropological parameter leads in many applications to the influence of the cardiogenic signal on the sum signal being better compensated by calculation compared to the embodiment in which the same cardiogenic reference signal section is used in each heartbeat.

For example, the signal processing unit generates different cardiogenic reference signal sections for different values or value ranges of the anthropological parameter. The signal processing unit subsequently selects a cardiogenic reference signal section as a function of the value of the anthropological parameter or averages over two cardiogenic reference signal sections.

The present invention further pertains to a ventilator with a signal processing unit according to the present invention. The ventilator uses the estimated respiratory signal, which the signal processing unit has determined, to ventilate a patient mechanically. In particular, the ventilator adapts the ventilation strokes which it performs automatically to the estimated respiratory signal.

The present invention further pertains to a computer program and to a signal sequence. In the process taking place on a signal processing unit, the computer program and the signal sequence cause the process according to the present invention to be carried out. The computer program is preferably stored permanently on a data storage medium. The signal sequence may also be downloaded via the Internet or an Intranet, without being permanently stored on a data storage medium. The signal processing unit can include any type of computer or processor configured/programmed based on the functions explained and detailed in the disclosure, preferably processor(s) for processing incoming signals. The hardware which may be a generic computer or microprocessor, such as multiple processors, a single processor or processors dispersed over a network, especially those adapted to perform the sequence of steps predominately used in signal processing. In this regard, the disclosure provides functions of the signal processing unit that are to be implemented using software with hardware to run it—such as a generic computer, a processor or a microprocessor.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing which sensors measure which different variables, which are used to determine the estimated respiratory signal $Sig_{res,est}$;

FIG. 11 is a view of a view with contour lines for the derivation of a modification function;

FIG. 12 is a view of an example for a modification function predefined in advance;

FIG. 13 is a view of a variation of the process, wherein only the attenuation function block is used, but the compensation function block is not;

FIG. 14a, 14b, 14c are a view of a comparison with a respective exemplary curve of the sum signal $Sig_{Sum}$ of the compensation signal $Sig_{com}$ and of the estimated respiratory signal $Sig_{res,est}$;

DESCRIPTION OF PREFERRED EMBODIMENTS

Figure 2:
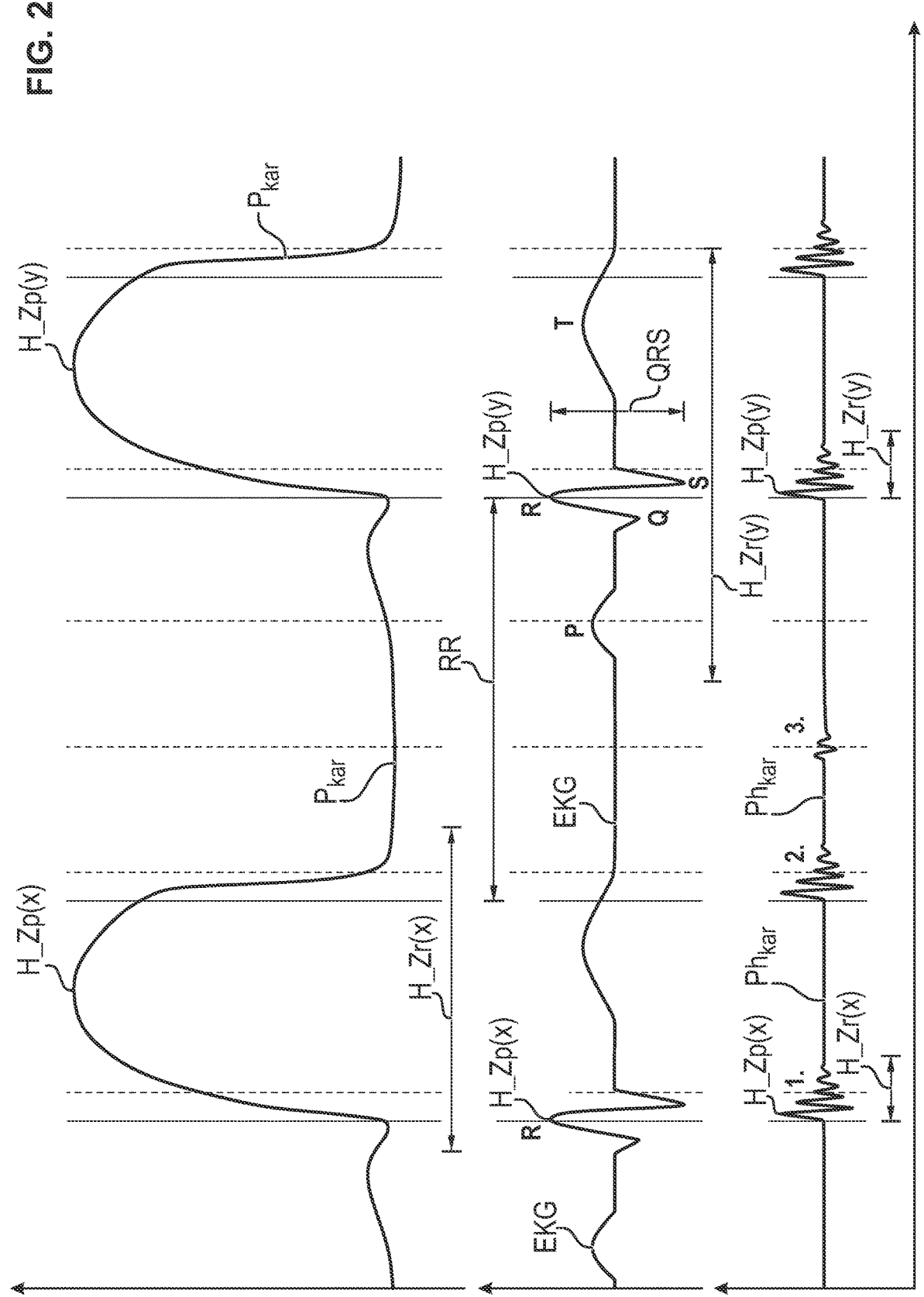
FIG. 2 is a view of three exemplary curves of the cardiogenic signal $Sig_{kar}$.

Referring to the drawings, the present invention is applied in the exemplary embodiment for the mechanical ventilation and/or for the monitoring of a patient.

A "signal" shall hereinafter be defined as the curve in the time range or also in the frequency range of a directly or indirectly measurable variable that is variable over time, which is correlated with a physical variable. This physical variable is related here to the cardiac activity and/or to the intrinsic breathing activity (spontaneous breathing and/or stimulated breathing) and/or to the other muscle activity of a patient and/or to the mechanical ventilation of the patient and is generated by at least one signal source in the body of the patient and/or by a ventilator. A "respiratory signal" is correlated with the intrinsic breathing activity and/or with mechanical ventilation of the patient, and a "cardiogenic signal" is correlated with the cardiac activity of the patient. A section of this signal, which is related to a defined time period, will hereinafter be called signal section. The value of a signal at a defined time is called the signal value or also signal section value.

The present invention is used in the exemplary embodiment to automatically determine an estimate $Sig_{res,est}$ for an electrical respiratory signal $Sig_{res}$, wherein the respiratory signal $Sig_{res}$ to be estimated is correlated with the intrinsic breathing activity of a patient P. The index "est" indicates that the signal is estimated. In one application of the exemplary embodiment, the patient P is ventilated mechanically at least at times, while the estimated respiratory signal $Sig_{res,est}$ is being determined. In another application, the present invention is used to monitor the patient P and to use the respiratory signal $Sig_{res}$ to be estimated for this patient, without the patient P being necessarily ventilated mechanically.

The breathing activity is elicited by electrical signals in the body of the patient P, and these electrical signals are determined approximately. Both the respiratory signal $Sig_{res}$ and the determined estimate $Sig_{res,est}$ are variable over time, i.e., $Sig_{res}=Sig_{res}(t)$ and $Sig_{res,est}=Sig_{res,est}(t)$.

This respiratory signal $Sig_{res}$ cannot be measured directly and isolated from other signals. On the one hand, especially if electrodes on the skin of the patient pick up measured values, it is not possible to measure directly signals generated in the body of the patient which "actuate" the respiratory muscles, but only electrical signals, which are generated during the contraction of the muscle fibers of the respiratory muscles. In addition, the electrical signals, which elicit, or cause, the intrinsic breathing activity of the patient P, are superimposed by electrical signals, which cause the cardiac activity of the patient P; more precisely, which electrical signals are generated during the contraction of the heart muscles. Therefore, only a sum signal $Sig_{Sum}$ can be measured directly after a corresponding processing of measured values. This sum signal $Sig_{Sum}$ is formed from a superimposition of the sought respiratory signal $Sig_{res}$, which is correlated with the breathing activity, and of a cardiogenic signal $Sig_{kar}$, which is correlated with the cardiac activity. This sum signal $Sig_{Sum}$ is, as a rule, superimposed by unwanted signals, which occur in the body of the patient and/or outside his body.

FIG. 1 schematically shows a mechanically ventilated patient P, a ventilator for the mechanical ventilation as well as a plurality of sensors, whose measured values are used as described below. The figure shows the mechanically ventilated patient P, the lungs Lu, the stomach Ma, the esophagus Sp and the diaphragm Zw of the patient P, an optional flexible measuring catheter 7, which is inserted into the esophagus Sp of the patient P and is used for a pressure measurement, a flexible connection piece 8, which is located in the mouth of the patient P during the mechanical ventilation and is connected to the optional measuring catheter 7, a ventilator 1, which is in a fluid connection with the patient P, ventilates the patient P mechanically at least from time to time and performs ventilation strokes in the process, four sets 2.1.1 through 2.2.2 of sensors with at least one respective measuring electrode each, wherein the measuring electrode sets 2.1.1 and 2.1.2 are arranged on the right and on the left of the sternum and which measuring electrode sets 2.2.1 and 2.2.2 are arranged at the costal arch, a measuring electrode, not shown, for the ground, a pneumatic sensor 3, which is located in space at a distance from the body of the patient P, an optional additional pneumatic sensor 17 at the ventilator 1, an optional sensor 4, which comprises an imaging device and an image analysis unit and is directed towards the thoracic region of the patient P, and an optional pneumatic probe 6 in the form of a probe or a measuring balloon in the esophagus and close to the diaphragm Zw of the patient P, wherein the probe 6 is in a fluid connection with the measuring catheter 7, an optional gastric probe 37 in the form of a measuring balloon, wherein the probe 37 is placed into the stomach Ma and is likewise in a fluid connection with the measuring catheter 7, optionally electrodes, not shown, in the esophagus of the patient P, and optionally a plethysmographic sensor, not shown, on the skin of the patient P, preferably an optically operating sensor.

The ventilator 1 comprises a display unit 18 and a signal processing unit 5, wherein the signal processing unit 5 has read access at least at times and write access at least at times to a memory 9.

The four measuring electrode sets 2.2.1 through 2.2.2 as well as the ground electrode, not shown, or also the esophageal electrodes, not shown, or the plethysmographic sensor supply—after signal processing—the sum signal $Sig_{Sum}$. The signal processing preferably comprises a so-called baseline filtering.

The pneumatic sensor 3 comprises in one embodiment a measuring transducer 3.1 with an opening, which is arranged in the vicinity of the mouth of the patient P and taps air from the fluid connection between the patient P and the ventilator 1. The tapped air is sent via a tube to a pressure sensor 3.2 of the sensor 3, which measures an indicator of the airway pressure $p_{aw}$ (pressure in airway) in the fluid connection and optionally an indicator of the volume flow Vol'. In one embodiment, the transducer 3.1 is arranged in or at a Y-piece close to the connection piece 8, i.e., close to the mouth of the patient P. Other embodiments of the pneumatic sensor 3 are likewise possible.

It is also possible to generate and use, e.g., a sum signal $Sig_{Sum}$ in the form of a mechanomyogram (MMG signal) instead of an electrical signal (EMG signal). Only the EMG or MMG sensors are needed for the exemplary embodiment. It is also possible to generate as the sum signal $Sig_{Sum}$ a signal that is correlated with the time curve describing the change in the blood volume in the body of the patient P, for example, by means of measured values that are obtained by optical plethysmography.

The optical sensor 4 measures the filling level of the lungs and/or the sitting position of the patient P, e.g., by image analysis.

An indicator $P_{aw}$ of the airway pressure and/or an indicator $P_{es}$ of the pressure in the esophagus Sp and/or an indicator $P_{ga}$ of the gastric pressure in the stomach Ma can be generated from the measured values of the other sensors, and a pneumatic indicator $P_{mus}$, which is likewise an indicator of the intrinsic breathing activity of the patient P, can be derived herefrom. By determining according to the present invention, on the one hand, an estimate $Sig_{res,est}$, and a pneumatic indicator $P_{mus}$, on the other hand, the intrinsic breathing activity of the patient P is determined with a higher reliability than in case of the derivation of only one signal, and it is possible to derive how well the respiratory muscle of the patient P converts electrical stimuli in the body of the patient P into pneumatic breathing activity (neuromechanical efficiency). The present invention can also be used in an embodiment in which the pneumatic indicator $P_{mus}$ is not used for the breathing activity even though the EMG signal or the MMG signal $Sig_{res,est}$ is.

The estimated respiratory signal $Sig_{res,est}$ determined according to the present invention is used, for example, for the following purposes:

- The neuromechanical efficiency of the breathing of the patient P is determined.
- the status of the respiratory muscles of the patient P is determined (determination of fatigue)—the pneumatic indicator $P_{mus}$ is not needed for this, asynchronies of the intrinsic breathing activity of the patient P are detected—the pneumatic indicator $P_{mus}$ is not needed for this, either,
- to monitor the patient P, the estimated respiratory signal $Sig_{res,est}$ and the respiratory EMG performance are determined and are outputted as two vital parameters in a form perceptible by a person, e.g., on the display unit 18, preferably visually in the form of a respective time curve, optionally together with the airway pressure $P_{aw}$ or with the esophageal pressure $P_{es}$ or with the gastric pressure $P_{ga}$,
- if the patient P is breathing spontaneously and/or his respiratory muscles are stimulated, i.e., the patient is not fully sedated, a support of the intrinsic breathing activity by a mechanical ventilation is triggered and/or carried out by a mechanical ventilation. For example, a pneumatic indicator $P_{mus}$ is derived for the intrinsic breathing activity of the patient P with the use of the respiratory signal $Sig_{res,est}$ and is used to ventilate the patient P mechanically by means of a ventilator. The ventilation strokes of the mechanical ventilation are carried out preferably as a function of the estimated respiratory signal $Sig_{res,est}$, preferably synchronized with the intrinsic breathing activity, which is described by the estimated respiratory signal respiratory signal $Sig_{res,est}$. For example, the ventilator 1 triggers the ventilation strokes as a function of the estimated respiratory signal $Sig_{res,est}$ and/or terminates them and/or specifies the respective amplitude of each ventilation stroke and/or the frequency of the ventilation strokes, which is variable over time, as a function of the estimated respiratory signal $Sig_{res,est}$. The end of the mechanical ventilation can also be regulated as a function of the estimated respiratory signal $Sig_{res,est}$.

To regulate the ventilator 1 during the mechanical ventilation of the patient P or to monitor the patient P and to use the estimated respiratory signal $Sig_{res,est}$ for the regulation or monitoring, the estimated respiratory signal $Sig_{res,est}$ is determined at a sufficiently high scanning frequency, i.e., the signal processing unit 5 provides a new signal value $Sig_{res,est}(t)$ for each scanning time. A high scanning frequency is defined such that there is a distance of less than 3 msec between two consecutive scanning times. The scanning frequency is preferably at least 1 kHz, especially preferably at least 2 kHz especially for the determination of fatigue. Some steps of the process described below are carried out, by contrast, at a lower scanning frequency, namely, at a frequency that is in the range of the heartbeat frequency, i.e., between 1 Hz and 2 Hz.

FIG. 2 shows as an example three typical time curves of the cardiogenic signal $Sig_{kar}$, namely, from top to bottom:

- A pneumatic signal $P_{kar}$ for the ventricular pressure, measured in Hg mm,
- an electrical EKG signal, measured in mV, as well as
- an acoustic signal $Ph_{kar}$ for the heart sounds, measured with an acoustic sensor.

The x axis applies to all three curves. The y axes pertain to the respective unit of measurement of the signal. The time is plotted on the x axis, and the respective value of the cardiogenic signal $Sig_{kar}$ on the y axis. The time period shown covers four consecutive heartbeats. In the EKG signal, each heartbeat comprises a so-called P wave, a QRS phase and a T wave.

For each time curve, the heartbeat time period H_Zr(x) and H_Zr(y) as well as the characteristic heartbeat times H_Zp(x) and H_Zp(y) of the two exemplary heartbeats No. x and No. y are shown for each time curve. For example, the R wave is used as the characteristic time H_Zp(x) of a heartbeat in the EKG signal. The distance RR between two consecutive heartbeats as well as the QRS amplitude QRS of a heartbeat are shown in FIG. 2. As is suggested in FIG. 2 and FIG. 19, the cardiogenic signal $Sig_{kar}$ is higher by several orders of magnitude than the respiratory signal $Sig_{res}$ in the range from the P wave to the T wave of a heartbeat and it is equal or smaller in the rest of the range. As is also seen in FIG. 2, how and especially with what length a heartbeat time period and a characteristic heartbeat time H_Zp(x), H_Zp(y), . . . are specified depends on the signal used. Different possible specifications are shown in FIG. 2.

Figure 3:
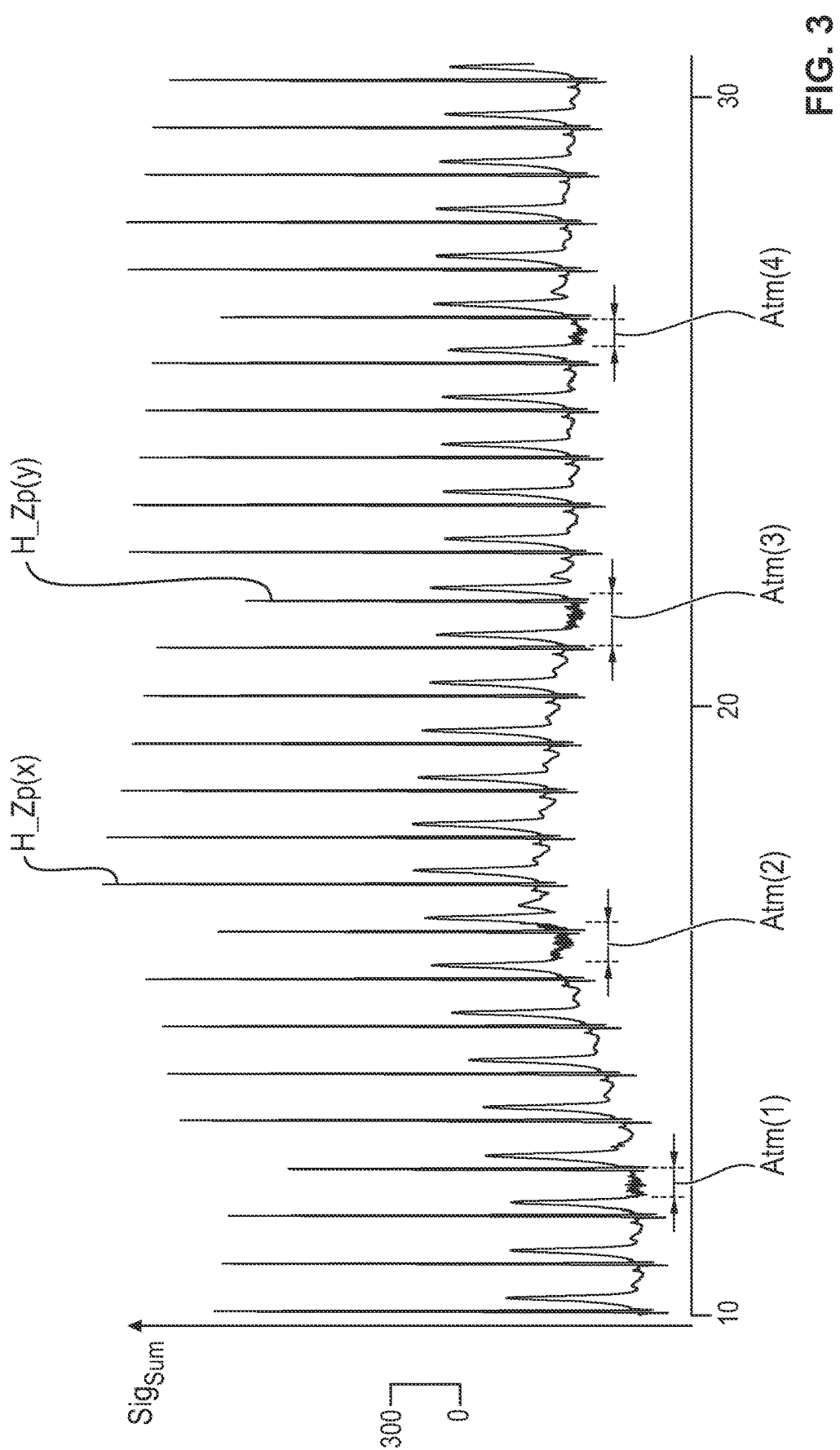
FIG. 3 is a view of an exemplary curve of the sum signal $Sig_{Sum}$.

FIG. 3 shows an exemplary time curve of the sum signal $Sig_{Sum}$ in a time period with four breaths and with a plurality of heartbeats. Four time periods Atm(1), Atm(4) of the four breaths and two characteristic heartbeat times H_Zp(x) and H_Zp(y) are shown. It can be seen that the cardiogenic signal $Sig_{kar}$ is several times higher in a heartbeat time period than the respiratory signal $Sig_{res}$ in this period. Outside a heartbeat time period, the respiratory signal $Sig_{res}$ is, however, sufficiently strong compared to the cardiogenic signal $Sig_{kar}$ and can therefore be determined from the sum signal $Sig_{Sum}$.

Figure 4:
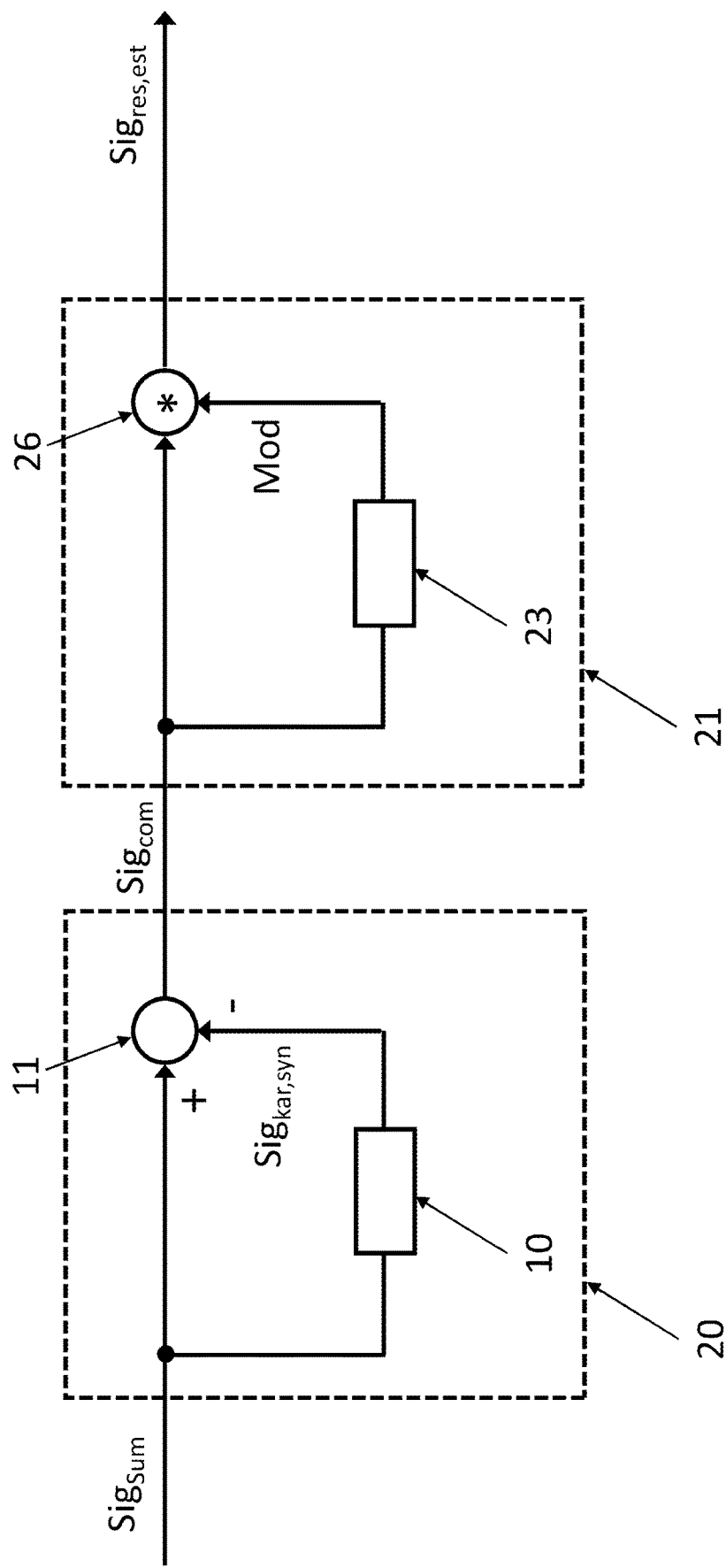
FIG. 4 is a view of the two function blocks for determining the estimated respiratory signal $Sig_{res,est}$.

FIG. 4 schematically shows two function blocks 20 and 21 of the signal processing unit 5, which perform each different signal processing steps in order to eliminate the cardiogenic signal $Sig_{kar}$ from the sum signal $Sig_{Sum}$ by calculation in order to compensate at least partially the influence of the cardiac activity on the measured sum signal $Sig_{Sum}$. The output signal of a compensation function block 20, namely, a compensation signal $Sig_{com}$ described below, is present as an input signal at an attenuation function block 21.

A functional unit 10 of the compensation function block 20 generates a synthetic cardiogenic signal $Sig_{kar,syn}$, which is an approximation (estimate) for the cardiogenic signal $Sig_{kar}$ and is composed of signal sections. The compensation function block 20 compensates the contribution of the synthetic cardiogenic signal $Sig_{kar,syn}$ to the sum signal $Sig_{Sum}$ by calculation, for example, by subtraction, and thereby generates the compensation signal $Sig_{com}$. Exemplary procedures for generating such a compensation signal $Sig_{com}$ are described in M. Ungureanu and W. M. Wolf: "Basic Aspects Concerning the Event-Synchronous Interference Canceller," *IEEE Transactions on Biomedical Engineering*, Vol. 53, No. 11 (2006), pp. 2240-2247, incorporated by reference, in L. Kahl and U. G. Hofmann: "Removal of ECG artifacts from EMG signals with different artifact magnitudes by template subtraction," *Current Directions in Biomedical Engineering*, 2019; 5(1), pp. 357-360, incorporated by reference, in DE 10 2007 062 214 B3/U.S. Pat. No. 8,109,269 B2, incorporated by reference, and in EP 3 381 354 A1, incorporated by reference.

The compensation function block 20 uses in one embodiment one of the procedures described there.

The compensation function block 20 uses in one embodiment one of the procedures described there.

Figure 5:
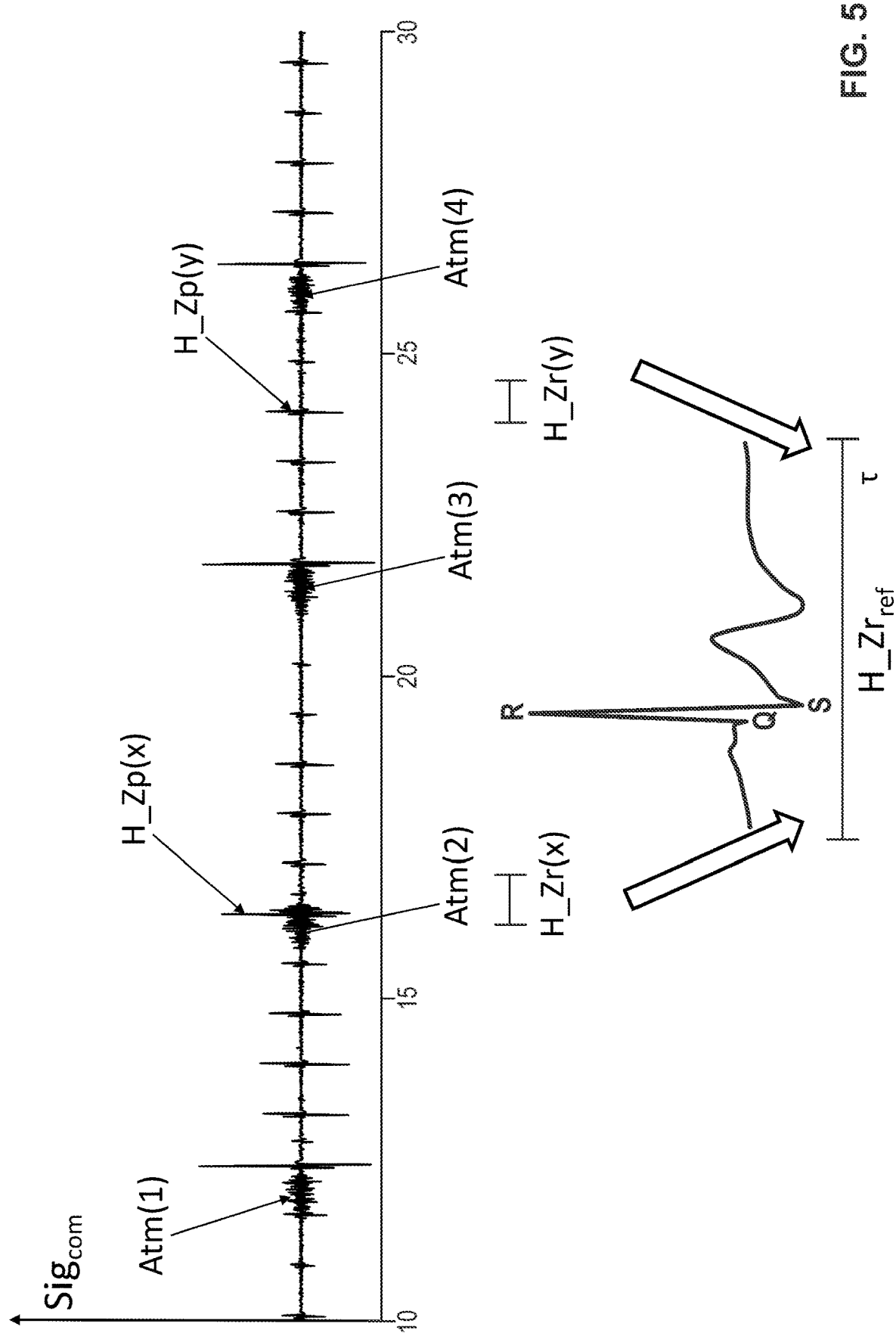
FIG. 5 is a view of an exemplary curve of the compensation signal $Sig_{com}$.

FIG. 5 shows an exemplary curve of the compensation signal $Sig_{com}$. This exemplary curve is formed by the compensation function block 20 as just described processing the sum signal $Sig_{Sum}$ shown as an example in FIG. 3. In addition, two exemplary heartbeat time periods/heartbeat times H_Zp(x) and H_Zp(y) are shown in FIG. 5.

A reference heartbeat time period $H\_Zr_{ref}$ is predefined. The time in the reference heartbeat time period $H\_Zr_{ref}$ is designated by τ. It is illustrated in FIG. 5 how these two heartbeat time periods/heartbeat times H_Zp(x) and H_Zp (y) are mapped to the same heartbeat time period $H\_Zr_{ref}$.

A functional unit 23 of the attenuation function block 21 generates from the compensation signal $Sig_{com}$ a modification signal section Mod described below, cf. FIG. 4 and FIG. 6. A functional unit 26 applies this modification signal section Mod to the compensation signal $Sig_{com}$, thereby bringing about by calculation a reduction of the electrical performance, especially an attenuation, and it generates thereby the estimated respiratory signal $Sig_{res,est}$.

Figure 6:
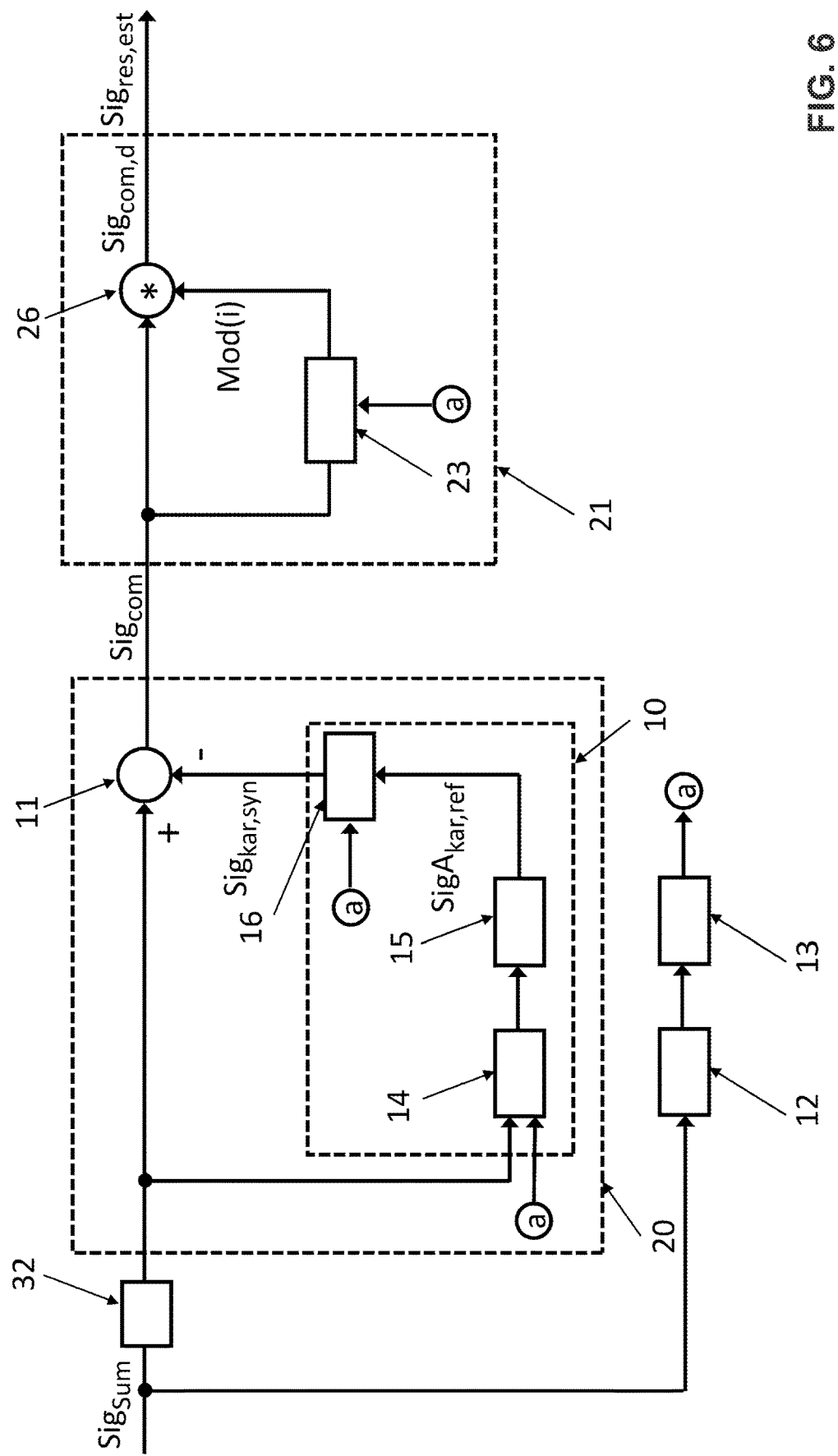
FIG. 6 is a view of the two function blocks from FIG. 4 in more detail, wherein a plurality of steps of the compensation function block are shown schematically.

FIG. 6 illustrates the steps of the compensation function block 20 in more detail The compensation function block 20 generates in an initialization phase a cardiogenic reference signal section $SigA_{kar,ref}$ which is stored in the memory, and it applies this cardiogenic reference signal section $SigA_{kar,ref}$ again in a subsequent use phase for each heartbeat. The following steps are carried out:

A functional unit 12 identifies in the sum signal $Sig_{Sum}$ the respective beginning and the respective end and/or the respective QRS phase of each heartbeat.

A functional unit 13 determines the respective exact heartbeat time H_Zp(x) of each heartbeat, doing so preferably with a tolerance of a few msec. The tolerance is especially preferably at most half the time period between two consecutive scanning times for the determination of the sum signal $Sig_{Sum}$, and this time period is preferably shorter than 1 msec.

The functional units 12 and 13 need a plurality of values of the sum signal $Sig_{Sum}$ for a plurality of consecutive scanning times in order to determine the exact heartbeat time H_Zp(x) of each heartbeat. In one embodiment, an optional functional unit 32 delays the sum signal $Sig_{Sum}$ for the next steps by a corresponding time period, cf. FIG. 6. The exact heartbeat time H_Zp(x) is available hereby in the next steps. This optional delaying functional unit 32 is omitted in the following figures. This delay is only applied if the respective application does not need the estimated respiratory signal $Sig_{res,est}$ in real time.

Furthermore, the following steps are carried out in the initialization phase:

A section $SigA_{Sum}(x)$ of the sum signal $Sig_{Sum}$ belongs to each heartbeat No. x, cf. FIG. 3.

A functional unit 14 superimposes by calculation the N sum signal sections $SigA_{Sum}(x_1), \ldots, SigA_{Sum}(x_N)$ for the last N heartbeats $x_1, \ldots, x_N$. When needed, these signal sections are cut by calculation to an identical length or compressed or stretched. A process for superimposing sections is described in M. Ungureanu and W. M. Wolf, loc. cit.

The N signal sections for the N heartbeats are preferably superimposed such that they have the same length and the R waves are one on top of another. Each signal section thus pertains to the same reference heartbeat time period $H\_Zr_{ref}$. A relative time in this reference heartbeat time period $H\_Zr_{ref}$ is designated by τ. A relative time τ=τ(t) corresponds to each absolute time t of the sum signal section $SigA_{Sum}(x)$ in this relative heartbeat time period. The functional unit 14 maps each sum signal section $SigA_{Sum}(x_1), \ldots, SigA_{Sum}(x_N)$ to the same reference heartbeat time period $H\_Zr_{ref}$. The designation "cardiac phase Φ" with a value range from 0° to 360° or of 0 to 2ττ can also be used instead of the "relative time" designation.

A functional unit 15 generates from the superimposition of N signal sections $SigA_{Sum}(x_1), \ldots, SigA_{Sum}(x_N)$ in the reference heartbeat time period $H\_Zr_{ref}$, which the functional unit 14 has generated, a cardiogenic reference signal section (template) $SigA_{kar,ref}$. This cardiogenic reference signal section $SigA_{kar,ref}$ approximately describes the curve of the cardiogenic signal $Sig_{kar}$ during a single heartbeat and it likewise relates it to the reference heartbeat time H_Zp(x) at τ=0. As was mentioned already, the cardiogenic component in the sum signal $Sig_{Sum}$ is several times larger than the respiratory component, and the respiratory components are "largely eliminated by averaging" by the averaging over N signal sections during a heartbeat if N is high enough. The functional unit 15 preferably applies a learning method to the N signal sections for the last N heartbeats. The cardiogenic reference signal section $SigA_{kar,ref}$ is preferably stored in the memory.

The following steps are carried out in the use phase:

The functional units 12 and 13 detect in the sum signal $Sig_{Sum}$ the heartbeats and determine the respective characteristic heartbeat time of each detected heartbeat, The cardiogenic reference signal section $SigA_{kar,ref}$ is used again for each heartbeat. In one embodiment, this is subtracted in an unchanged form from the sum signal section $SigA_{kar,ref}$ (template subtraction).

A functional unit 16 optionally uses, by contrast, the value of at least one anthropological parameter, which influences the cardiac activity and hence the cardiogenic signal $Sig_{kar}$ and has been measured at this heartbeat No. x. The filling level of the lungs and an indicator of the posture of the patient P as well as the distance RR between the R waves of two consecutive heartbeats are examples of such an anthropological parameter. The functional unit 16 fits for each heartbeat the cardiogenic reference signal section $SigA_{kar,ref}$ to the parameter value or each parameter value measured at this heartbeat and generates thereby a cardiogenic signal section $SigA_{kar}(x)$.

The functional unit 16 positions the cardiogenic reference signal section $SigA_{kar,ref}$ or optionally the adapted cardiogenic signal section $SigA_{kar}(x)$ relative to the sum signal section $SigA_{Sum}(x)$ of the current heartbeat with the correct time, e.g., in a QRS-synchronized manner. A new synchronized section $SigA_{kar,syn}(x)$ of the synthetic cardiogenic signal $Sig_{kar,syn}$ is generated thereby. The synthetic cardiogenic signal $Sig_{kar,syn}$ is preferably outputted in a form perceptible by a person, e.g., on the output unit 18.

A functional unit 11 compensates in the newest sum signal section $SigA_{Sum}(x)$ the influence of the cardiogenic signal $Sig_{kar}$, for example, by subtracting the cardiogenic reference signal section $SigA_{kar,ref}$ or the adapted cardiogenic signal section $SigA_{kar}(x)$ from the newest sum signal section $SigA_{Sum}(x)$.

A preferred embodiment for applying a learning method in the initialization phase as well as the respective value of an anthropological parameter in the use phase for each heartbeat is described in the subsequently published German Unexamined Patent Application No. DE 10 2019 006 866 A1, incorporated by reference.

At the beginning of the process, i.e., after the patient P has been connected to the measuring electrodes 2.1.1 through 2.2.2, the initialization phase is carried out, which covers a time period of N heartbeats. As was described above, the compensation function block 20 generates during the initialization phase an initial cardiogenic reference signal section $SigA_{kar,ref}$ as a function of the sum signal sections $SigA_{Sum}(x_1), \ldots, SigA_{Sum}(x_N)$ for the last N heartbeats. The compensation function block 20 adapts during the process the cardiogenic reference signal section $SigA_{kar,ref}$ to the respective last N heartbeats and stores it in the memory 9. The steps in the initialization phase and the adaptation to the respective last N heartbeats are preferably carried out with the low scanning frequency, which is approximately equal to the heartbeat frequency.

The sections for a heartbeat are preferably superimposed with twice the time resolution of the sum signal $Sig_{Sum}$. This means that the values of the sum signal $Sig_{Sum}$ are determined with a high scanning frequency f, i.e., the distance $\Delta t$ between two scanning times is $1/f$. The time resolution is increased by calculation to, e.g., 2f or 3f, e.g., by positioning, by calculation, a signal value $Sig_{Sum}(t+\Delta t/2)$, for example, by interpolation, between two signal values $Sig_{Sum}(t)$ and $Sig_{Sum}(t+\Delta t)$ derived from measured values.

The following steps are carried out with a high scanning frequency (few msec or even only a few tenths of 1 msec) after the initialization phase):

The signal processing unit 5 derives a respective new value $Sig_{Sum}(t)$ for the sum signal $Sig_{Sum}$ from the measured values.

The functional units 12 and 13 detect in the sum signal $Sig_{Sum}$ the beginning or the exact characteristic time $H\_Zp(x)$ of a heartbeat x and thereby determine a new sum signal section $SigA_{Sum}(x)$.

The compensation function block 20 optionally adapts the cardiogenic reference signal section $SigA_{kar,ref}$ to the respective value of at least one anthropological parameter, determines the associated relative time $\tau=\tau(t)$ and generates by positioning with the correct time an additional signal section, namely, the chronologically newest section $SigA_{kar,syn}(x)$ of the synthetic cardiogenic signal $Sig_{kar,syn}$.

The functional unit 11 subtracts from the new value $Sig_{Sum}(t)$ the value $SigA_{kar,ref}[\tau(t)]$ or $SigA_{kar}(x)[\tau(t)]$ of the cardiogenic reference signal section $SigA_{kar,ref}$ or of the adapted cardiogenic signal section $SigA_{kar}(x)$ for the same relative time $\tau$, i.e., $$Sig_{com}(t) = Sig_{Sum}(t) - SigA_{kar,syn}[\tau(t)]$$

or it compensates in another manner the cardiogenic influence, for example, by means of a high-pass filter or by an Independent Component Analysis or by a so-called blind source separation, which is described, for example, in DE 10 2015 015 296 A1.

The compensation function block 20 outputs a new signal section $SigA_{com}(x)$ for the compensation signal $Sig_{com}$.

The synthetic cardiogenic signal $Sig_{kar,syn}$ is not, as a rule, identical to the actual cardiogenic signal $Sig_{kar}$. The essential reasons are the following:

The heartbeat is not, as a rule, an ideal periodic process.

The breathing does not take place synchronously with the heartbeat.

Even though the cardiogenic signal $Sig_{kar}$ is markedly stronger in each heartbeat than the respiratory signal $Sig_{res}$, the respiratory signal $Sig_{res}$ also acts in a heartbeat time period on the sum signal $Sig_{Sum}$.

A new signal value is needed quasi in real time, for example, when the estimated respiratory signal $Sig_{res,est}$ is used to regulate the ventilator 1. The following additional problem arises here. The newest section $SigA_{kar,syn}(x)$ of the synthetic cardiogenic signal $Sig_{kar,syn}$ can only be positioned with the correct time with sufficient accuracy if the exact heartbeat time $H\_Zp(x)$ has been detected. This is, however, true, as a rule, only if the R wave of this heartbeat has been detected. The newest section $SigA_{Sum}(x)$ cannot be positioned exactly with the correct time during the time period between the beginning of a heartbeat and the R wave, but it can only be positioned in time in an estimated manner. The process according to the present invention reduces the influence of a position not carried out exactly with the correct time, especially because the exact position in time is not needed in a next step.

In addition, a process noise and/or a measurement noise always act on the process of estimating the cardiogenic signal $Sig_{kar}$ by the synthetic cardiogenic signal $Sig_{kar,syn}$.

The attenuation function block 21 is used in the exemplary embodiment for the reasons mentioned to finish the compensation signal $Sig_{com}$. This finishing reduces especially the effect of an only inaccurate positioning in time of the newest section $SigA_{kar,syn}(x)$ of the synthetic cardiogenic signal $Sig_{kar,syn}$ before the exact heartbeat time $H\_Zp(x)$ is detected. In addition, the heartbeat of a person is often irregular, and especially the frequency and/or the amplitude of the heartbeat vary over time. The compensation function block 20 cannot fully compensate this irregularity by calculation in many cases.

A finishing of a sum signal $Sig_{Sum}$ is also described, e.g., in S. Abbaspour and A. Fallah: "A Combination Method for Electrocardiogram Rejection from Surface Electromyogram," *Open Biomedical Engineering Journal*, Vol. 8 (2014), pp. 13-19, incorporated by reference. Even though the embodiment according to the present invention, which will be described below, can be used together with a threshold value, it avoids especially the need to specify a threshold value in advance, which need arises there.

Figure 7:
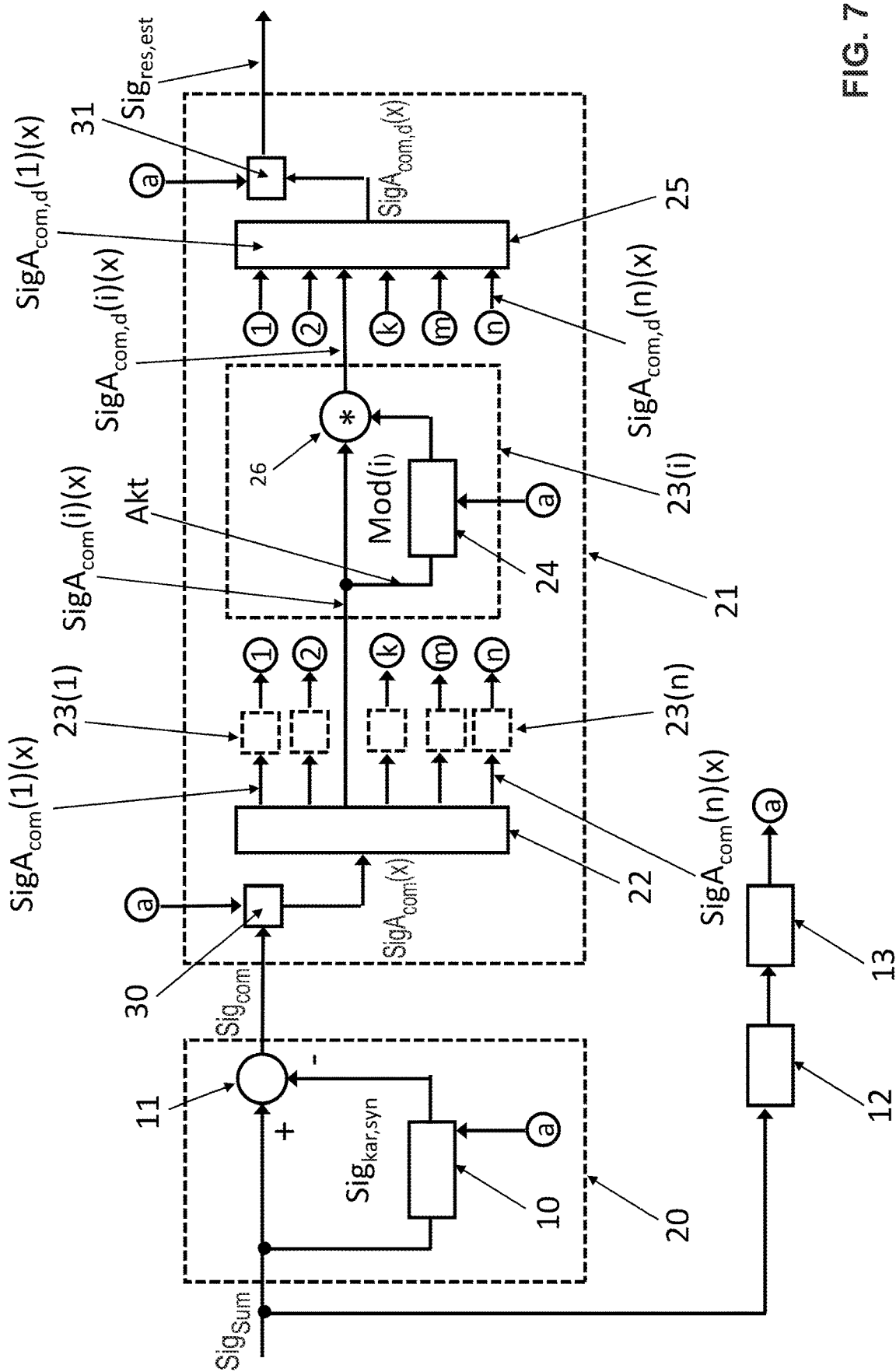
FIG. 7 is a view of the two function blocks from FIG. 4 in an even greater detail, where the decomposition, the attenuation and the composition by the attenuation function block 21 are shown schematically.

FIG. 7 illustrates the steps described below, which are carried out by the attenuation function block 21. The compensation signal $Sig_{com}$ is present at the attenuation function block 21.

A functional unit 30 generates the compensation signal section $SigA_{com}(x)$ for the newest detected heartbeat x from the compensation signal $Sig_{com}$. It uses for this the characteristic heartbeat time H_Zp(x) and the heartbeat time period H_Zr(x), which the functional units 12 and 13 have detected with the use of the sum signal $Sig_{Sum}$.

A functional unit 22 decomposes the compensation signal section $SigA_{com}(x)$ of the compensation signal $Sig_{com}$ into n signal component sections $SigA_{com}(1)(x), \ldots, SigA_{com}(n)(x)$ for n frequency bands, preferably by means of a wavelet transformation. Here, n is a predefined number, and the frequency bands are preferably disjunct. The value of n is preferably between 5 and 10 and it especially preferably equals 8. If the signal component sections $SigA_{com}(i)(x)$ are joined together and combined with the correct time, a signal component $Sig_{com}(i)$ is formed.

A respective functional unit 23(*i*) is applied for each frequency band i to the signal component section $SigA_{com}(i)(x)$, i=1, ..., n. The functional unit 24 of the exemplary functional unit 23(*i*) generates a modification signal Mod(i), which represents a time curve, wherein the modification signal Mod(i) covers a relative heartbeat time period T and each signal value Mod(i)(τ) is a number between 0 and 1 (inclusive). Consequently, a modification signal Mod(i) is generated for each level i in the initialization phase. The arrow "Akt" suggests that the modification signal Mod(i) is continually updated in the use phase as well. This updating is eliminated in the modification shown in FIG. 12.

A functional unit 26 applies in the use phase the modification signal Mod(i) positioned with correct time to the signal component section $SigA_{com}(i)(x)$ for the heartbeat x and generates the attenuation signal component section $SigA_{com,d}(i)(x)$ (i=1, ..., n). For example, the functional unit 26 multiplies the two signal values $SigA_{com}(i)(x)(t)$ and Mod(i)[τ(t)] by one another and thereby generates for each scanning time t a value $SigA_{com,d}(i)(x)(t)$ of the attenuation signal component section $SigA_{com,d}(i)(x)$, for example, according to the calculation instruction $$SigA_{com,d}(i)(x)(t) = SigA_{com}(i)(x)(t) * Mod(i)[\tau(t)].$$

This modification brings about an attenuation of the signal component section $SigA_{com,d}(i)(x)$. The sign of each signal value $SigA_{com}(i)(x)(t)$ is maintained during the attenuation. Alternative embodiments of the attenuation will be described farther below.

Figure 8:
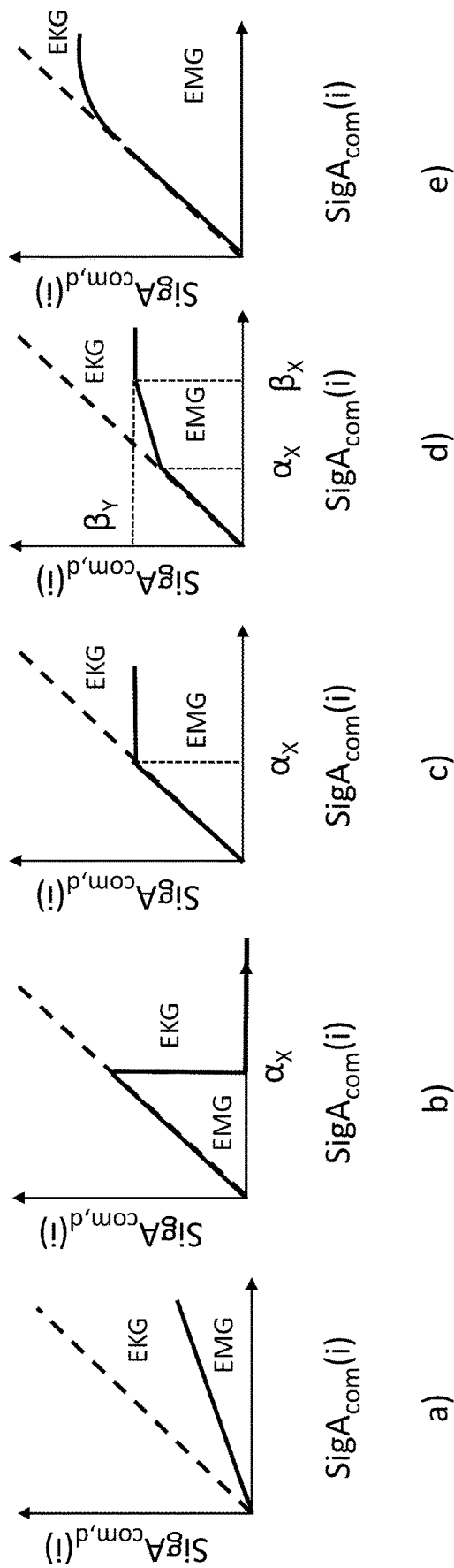
FIG. 8 is a view of a plurality of exemplary components of a modification function.

FIG. 8 illustrates five alternative possibilities of how the attenuation signal component section $SigA_{com,d}(i)(x)$ is generated by attenuation from the signal component section $SigA_{com}(i)(x)$. The signal component section $SigA_{com}(i)(x)$ is divided by the attenuation through the calculation into a respiratory component $SigA_{com,d}(i)$, which is also designated as EMG in FIG. 8, and into a cardiogenic component, which is designated as EKG.

Possibility a) is the embodiment just described, multiplication by a factor Mod(i), wherein the slope Mod(i)[τ(t)] of the straight line depends on τ(t). Possibility b) means a hard threshold value (hard threshold) α, wherein this threshold value α=α[(τ(t)] likewise depends on τ(t). Possibility c) means a soft threshold value (soft threshold). Possibility d) is a mixed form of a) and c). Possibility e) will be described farther below.

Consequently, an attenuation signal component section $SigA_{com,d}(i)(x)$, which is related to the time period H_Zr(x) of the last heartbeat, is generated by the modification.

The functional unit 25 combines the attenuation signal component sections $SigA_{com,d}(1)(x), \ldots, SigA_{com,d}(n)(x)$ into an attenuation signal component section $SigA_{com,d}(x)$, cf. FIG. 7, where the functional unit 25 preferably performs a wavelet back transformation (inverse wavelet transformation), and outputs this attenuation signal component section $SigA_{com,d}(x)$ as an output signal.

The functional unit 31 generates the sought estimated respiratory signal $Sig_{res,est}$. It uses for this the characteristic heartbeat times H_Zp(x), the heartbeat time periods H_Zr(x) and the attenuation signal component sections $SigA_{com,d}(x)$. For example, the section of the estimated respiratory signal $Sig_{res,est}$ is equal in each heartbeat time period H_Zr(x) to the sections $SigA_{com,d}(x)$ for this heartbeat time period H_Zr(x). For a section that is located between two consecutive heartbeat time periods H_Zr(x) and H_Zr(x+1), the functional unit 31 preferably uses the corresponding section of the compensation signal $Sig_{com}$ as a section of the estimated respiratory signal $Sig_{res,est}$ and interpolates when needed. The functional unit 31 outputs the respiratory signal $Sig_{res,est}$ estimated in this manner.

FIG. 4, FIG. 6 and FIG. 7 show an embodiment in which the compensation function block 20 generates from the sum signal $Sig_{Sum}$ the compensation signal $Sig_{com}$ and the attenuation function block 21 generates from the compensation signal $Sig_{com}$ the estimated respiratory signal $Sig_{res,est}$. FIG. 13 shows an alternative embodiment, in which only the attenuation function block 21 is used and the sum signal $Sig_{Sum}$ is used directly as the input signal for the attenuation functions block 21.

FIG. 14 shows a comparison with an exemplary curve of the sum signal $Sig_{Sum}$ (FIG. 14a), of the compensation signal $Sig_{com}$ (FIG. 14b) and of the estimated respiratory signal $Sig_{res,est}$ (FIG. 14c).

The attenuation function block 21 will be described in more detail below. The attenuation function block 21 eliminates a noise in the compensation signal $Sig_{com}$ by calculation by means of an attenuation signal. Contrary to other processes, e.g., to that described in S. Abbaspour and A. Fallah, loc. cit., the embodiment according to the present invention needs no cardiogenic signal $Sig_{kar}$ to determine the estimated respiratory signal $Sig_{res,est}$ from the sum signal $Sig_{Sum}$, and in particular, no cardiogenic signal $Sig_{kar}$ determined by means of measured values. It is often just as impossible to determine such a cardiogenic signal $Sig_{kar}$ as the sought respiratory signal $Sig_{res}$. In addition, the step of applying a binary threshold value, i.e., to set signal values above or below a predefined threshold value to zero, is not necessary when the attenuation function block 21 according to the present invention is used. The attenuation according to the present invention of a value of the compensation signal $Sig_{com}$ depends, in addition, on the relative reference time τ, which leads to a better compensation of the cardiogenic signal $Sig_{kar}$ than, for example, an attenuation averaged over the entire heartbeat time period. Moreover, a plurality of frequency bands are preferably used because the compensation signal $Sig_{com}$ is attenuated, as a rule, differently in different frequency bands.

In the initialization phase for the attenuation, which extends over M heartbeats, the attenuation function block 21 calculates n reference modification signal sections Mod(1), Mod(n). The attenuation function block 21 updates these n reference modification signal sections Mod(1), . . . , Mod(n) continuously during the subsequent use phase as a function of the last M heartbeats and stores them in the memory 9. The numbers M (number of heartbeats used for the updating) and N (number of heartbeats for calculating the cardiogenic reference signal section $SigA_{kar,ref}$) may be equal or differ from one another.

The functional unit 22 of the attenuation function block 21 from FIG. 7 and FIG. 13 carries out a wavelet transformation, preferably a stationary wavelet transformation or a transformation á trous, in order to decompose the newest section $SigA_{com}(x)$ of the compensation signal $Sig_{com}$ into n newest sections $SigA_{com}(1)(x), \ldots, SigA_{com}(n)(x)$. Wavelet transformations are described, for example, in W. Bäni: "Wavelets—An introduction for engineers," Oldenbourg, 2002, incorporated by reference. A stationary wavelet transformation has a lower variance against a shift in time than the alternatively usable discrete wavelet transformation. It is also possible to use a "Short Time Fourier Transformation:" or an "Empirical Mode Decomposition" instead of a wavelet transformation.

In a preferred embodiment of a wavelet transformation, n frequency bands are predefined, which are called "levels" in a wavelet transformation. Level 1 belongs to the frequency band with the highest frequencies, level n to the frequency band with the lowest frequencies. A respective wavelet function $$\psi_{s(i),a(i)}(t) = \frac{1}{s(i)^{\frac{1}{2}}} \psi\left(\frac{t-a(i)}{s(i)}\right)$$

belongs to each level i (i=1, n), with a predefined basic function ("mother wavelet") W, with a predefined compression s(i) and with a predefined shift a(i), wherein the level 1 has the greatest compression and level n the lowest compression, i.e., $s(1) \leq s(2) \leq \ldots \leq s(n)$. It is possible that the shift does not depend on the level, i.e., $a(1)=a(2)=\ldots a(n)$. The n signal component sections $SigA_{com}(1)(x)$, $SigA_{com}(n)(x)$ are generated step by step in this order, i.e., the signal component $SigA_{com}(1)(x)$ is generated first for the first level. For example, the db5 wavelet (db=Daubechies), also called "Daubechies wavelet with 5 vanishing moments," is used as the basic function Ψ.

The attenuation function block 21 comprises the functional unit 22 for the decomposition, a functional unit 25 for the back transformation as well as a functional unit 23(i) and two functional units 24 and 26 for each level i.

The functional units 14 and 15 from FIG. 6 update the cardiogenic reference signal section $SigA_{kar,ref}$ as soon as an additional heartbeat has concluded, i.e., they generate an adapted cardiogenic signal section $SigA_{kar}(x)$. In addition, the functional unit 23(i) updates the reference modification signal sections Mod(i) for the n levels as soon as the additional heartbeat has concluded (i=1, . . . , n).

In one embodiment, the functional unit 24 from FIG. 7 and FIG. 13 performs the steps described below for each level i and for each signal component section $SigA_{com}(i)(x)$ of a heartbeat x (i=1, . . . , n):

The functional unit 24 determines in the initialization phase an average signal section $Pow_{com,av}(i)$ for the time curve of an electrical performance or power, where the time curve covers a single relative heartbeat time period T and wherein averaging is carried out in a certain manner over the M signal component sections $SigA_{com}(i)$ of M heartbeats. It is possible to weight the more recent heartbeats more greatly than the older heartbeats. For example, $Pow_{com}(i)(\tau)=Abs[SigA_{com}(i)(\tau)]$ (the absolute value)

or $Pow_{com}(i)(\tau)=RMS[SigA_{com}(i)(\tau)]$ (root mean square, RMS, the effective value).

As a result, M performance/power signal sections $Pow_{com}(i)$ are calculated for the M heartbeats in the initialization phase. Each performance signal section $Pow_{com}(i)$ is preferably calculated with the use of a suitable filter, and smoothing is performed in a suitable manner over the values of the compensation signal $Sig_{com}$. Each performance signal section $Pow_{com}(i)$ covers a relative heartbeat time period T each. The functional unit 24 superimposes the M performance signal sections $Pow_{com}(i)$ synchronously to the heartbeats, maps them, for example, to the reference heartbeat time period $H\_Zr_{ref}$, and then averages over the superimposed M sections. An average performance signal section $Pow_{com,av}(i)$, which is an indicator of the average electrical performance of the compensation signal $Sig_{com}$ during a relative heartbeat time period T, is determined for level No. i, wherein the determined average electrical performance depends on the relative reference time T, i.e., it varies over time. Influencing factors, which do not originate from the cardiac activity of the patient P but from the breathing activity, for example, coughing or clearing the throat, are "eliminated by averaging."

Figure 15:
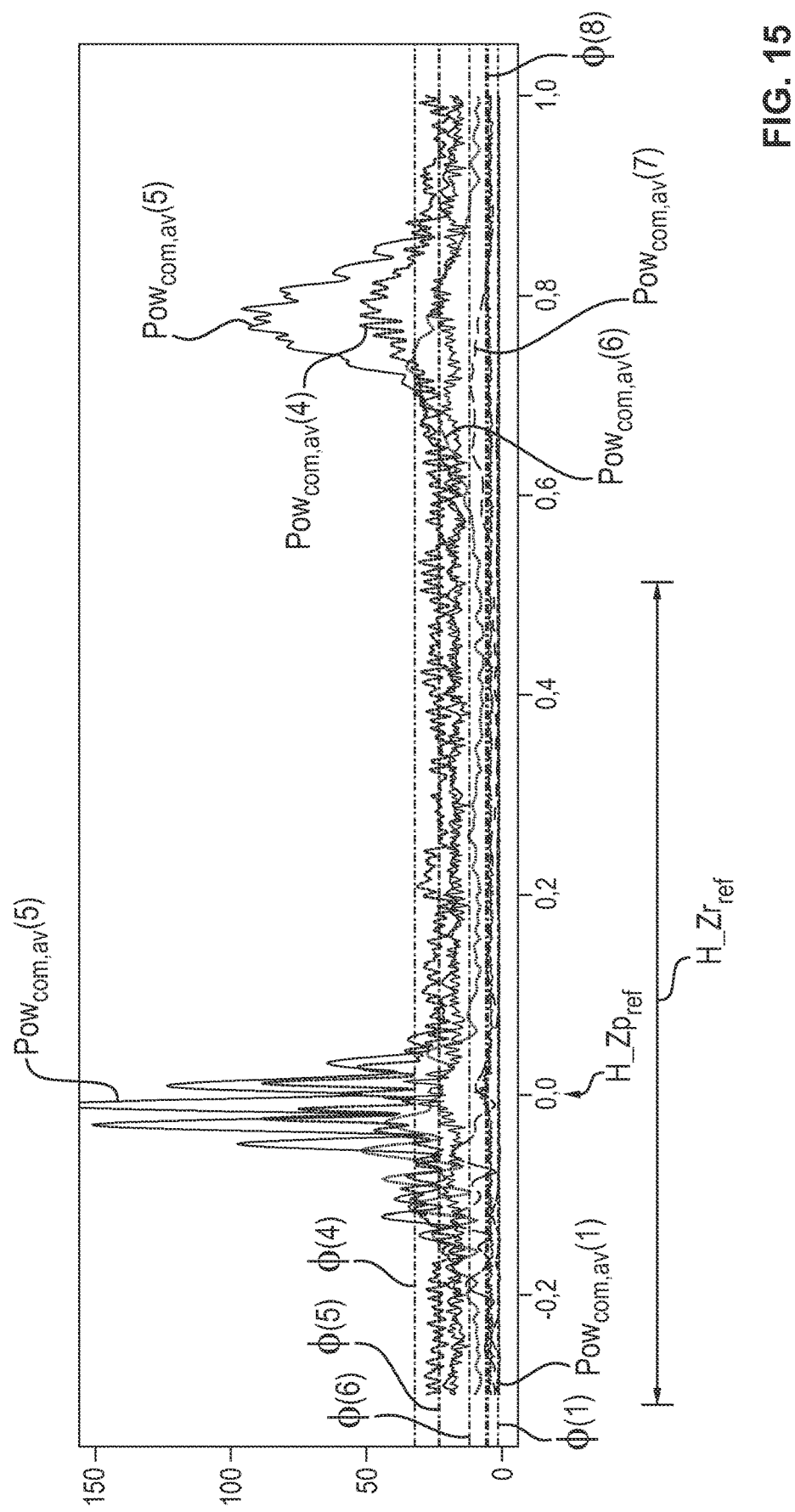
FIG. 15 is a view of an average performance/power signal sections $Pow_{com,av}(1), \ldots, Pow_{com,av}(n)$ and calculated threshold values $\varphi(1), \ldots, \varphi(n)$ for the n frequency bands (levels)

FIG. 15 shows the reference heartbeat time period $H\_Zr_{ref}$ as well as the reference heartbeat time $H\_Zp_{ref}$ of this average performance signal section $Pow_{com,av}(i)$ generated by heartbeat-synchronous superimposition. Eight different levels, i.e., n=8, are distinguished in this example. The time t=0 on the x axis was decomposed into the reference heartbeat time $H\_Zr_{ref}$. Furthermore, FIG. 15 shows the n=8 average performance signal sections $Pow_{com,av}(1), \ldots, Pow_{com,av}(8)$ for the n=8 levels.

Figure 16:
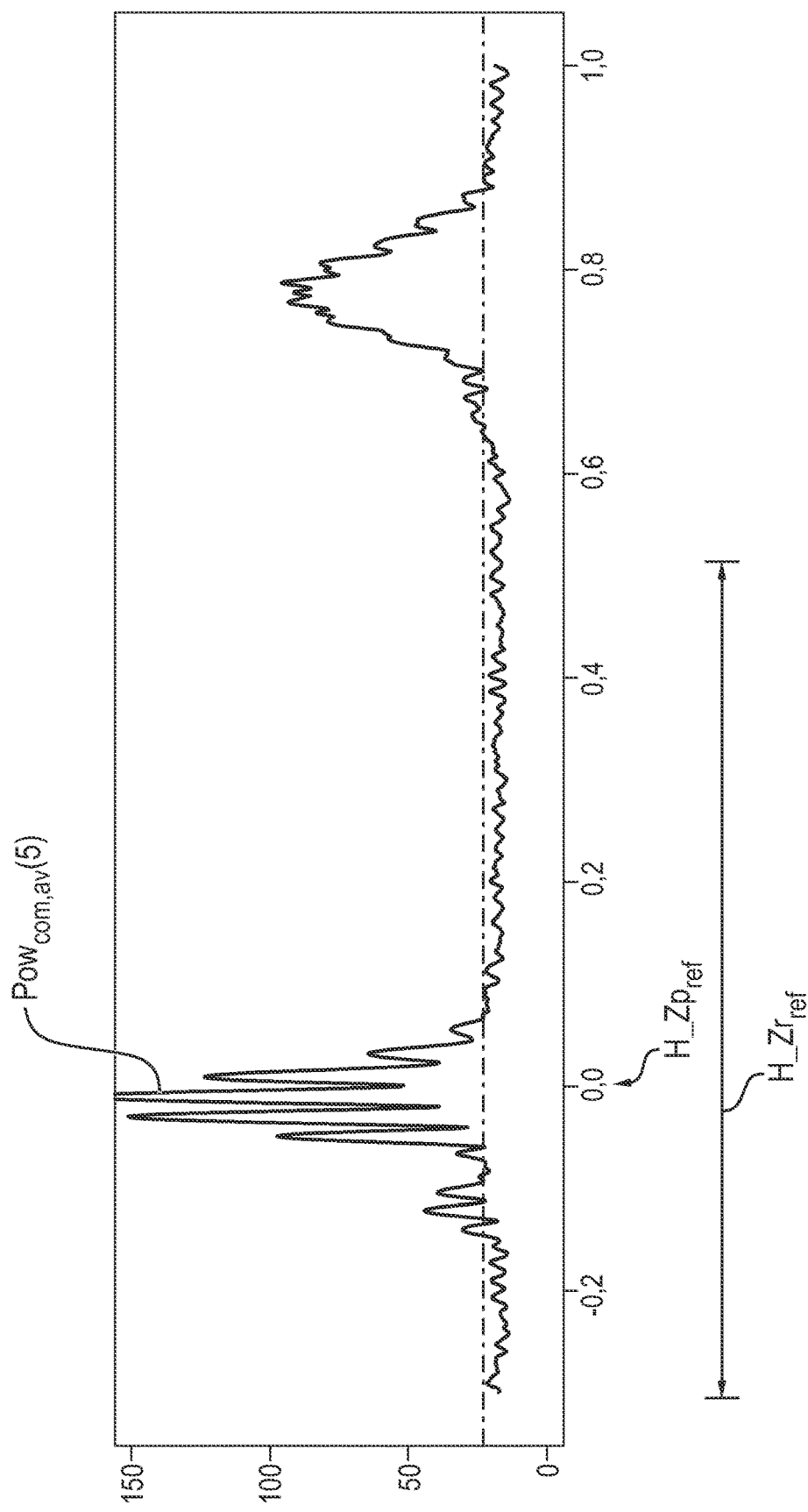
FIG. 16 is a view of an average performance/power signal section $Pow_{com,av}(5)$ for level No. 5.

FIG. 16 shows the average performance signal section $Pow_{com,av}(5)$ for level No. 5.

A mean signal value Avg(i) and, with the use of the mean signal value Avg(i), a threshold value (threshold) Φ(i) are derived from the average performance signal section $Pow_{com,av}(i)$ for level No. 1. The mean signal value Avg(i) and the threshold value Φ(i) vary, as a rule, from level i1 to level i2 and also for a single level i from heartbeat to heartbeat when the mean signal value Avg(i) and the threshold value φ(i) are continually updated as a function of the respective latest M heartbeats. A noise in the compensation signal $Sig_{com}$ is later eliminated at least partially by means of this threshold value φ(i), which depends on the compensation signal $Sig_{com}$, wherein this noise is generated essentially by the cardiogenic signal $Sig_{kar}$. Thanks to the procedure just described, the threshold values (D(i) are calculated for the run time and do not need to the predefined.

The average signal value Avg(i) is calculated, for example, as an arithmetic mean or also as a median over R signal values of the average performance signal component $Pow_{com,av}(i)$ at R consecutive relative scanning times $\tau_1, \ldots, \tau_R$ of the reference heartbeat time $H\_Zr_{ref}$. The median is less sensitive to freak values than the arithmetic mean, but its calculation requires more computing time.

To calculate the threshold value Φ(i), a factor α is predefined, for example, α=2. The threshold value φ(i) is calculated, for example, according to the calculation instruction $\varphi(i) = [1+n-i)/\alpha * n] * Avg(i)$.

FIG. 15 shows, furthermore, the n threshold values Φ(1), . . . , Φ(n) for the n levels.

The higher the signal value $Pow_{com,av}(i)(\tau)$ of the average performance signal section $Pow_{com,av}(i)$ at the corresponding relative time $\tau(t)$ of the reference heartbeat time period $H\_Zr_{ref}$, the more greatly shall a signal value $SigA_{com}(i)(x)(t)$ of the signal component $SigA_{com}(i)(x)$ of the compensation signal $Sig_{com}$ be attenuated, since high signal values originate from the cardiogenic signal $Sig_{kar}$ based on the averaging over N heartbeat time periods. The attenuation consequently depends on the currently determined sum signal $Sig_{Sum}$ rather than on a threshold value determined in advance. As was mentioned already, the attenuation according to this embodiment depends, in addition, on the relative time $\tau$ during a reference heartbeat time period $H\_Zr_{ref}$. The attenuation can be adapted in this manner to the current cardiac activity of the patient P, even in case of irregularities in the cardiac activity.

In one embodiment, a reference modification signal section $Mod(i)$ is generated from the average performance signal section $Pow_{com,av}(i)$, for example, according to the following calculation instruction:

$$Mod(i)(\tau) = \min\{Avg(i)/Pow_{com,av}(i)(\tau), 1\},$$

if $\tau$ is in the reference heartbeat time period $H\_Zr_{ref}$ and $Pow_{com,av}(i)(\tau) > \varphi(i)$, and $Mod(i)(\tau) = 1$ otherwise.

Each signal value $Mod(i)(\tau)$ of the reference modification signal section $Mod(i)$ is a number between 0 and 1 (inclusive).

The embodiment in which the signal value $Mod(i)(\tau)$ is set at 1 outside the reference heartbeat time period $H\_Zr_{ref}$ ensures that the reference modification signal section $Mod(i)$ brings about an attenuation for the current heartbeat only.

In a generalization, each value for $Mod(i)$ is calculated according to the calculation instruction $$Mod(i)(\tau) = \min\{F[Pow_{com,av}(i)(\tau)], 1\},$$

wherein $F = F(u)$ is a function falling in u (the greater u is, the lower is $F(u)$) and has a value range from 0 to y, wherein y is greater than or equal to 1.

As is shown in FIG. 8, there are alternatives to the embodiment to achieve the attenuation by a multiplication. A threshold value $\alpha_x = \alpha_x(\tau)$ is used in a plurality of embodiments that are shown in FIG. 8 b) through FIG. 8 d). In one embodiment, which is shown in FIG. 8 d), two additional threshold values $\beta_x = \beta_x(\tau)$ and $\beta_y = \beta_y(\tau)$ are additionally used.

In one form of the embodiment according to FIG. 8 d), parameters p1, p2, p3 and p4 are predefined. Preferably p1<p2<p3. For example, p1=0.8, p2=1, p3=1.1 as well as $p_4=1.2$ or even $p_1=1$, $p_2=1.2$, $p_3=\pi/2$ as well as $p_4=1.8$.

$$\alpha_x(\tau) = p_1 * \min\{Avg(i)/Pow_{com,av}(i)(\tau), p_4\}$$

$$\beta_x(\tau) = p_2 * \min\{Avg(i)/Pow_{com,av}(i)(\tau), p_4\}$$

$$\beta_y(\tau) = p_3 * \min\{Avg(i)/Pow_{com,av}(i)(\tau), p_4\}.$$

In one form of the embodiment according to FIG. 8 b) and FIG. 8 c), parameters $p_1$ and $p_4$ are predefined, e.g., $p_1=1.5$ as well as $p_4=0.8$. Now, $$\alpha_x(\tau) = p_1 * \min\{Avg(i)/Pow_{com,av}(i)(\tau), p_4\}.$$

FIG. 8 a) through FIG. 8 d) show the modification for positive values of $SigA_{com}(i)(t)$ only. However, the attenuation does not preferably change the sign. Attenuation is preferably carried out therefore as follows:

$$SigA_{com,d}(i)(t) = sign(SigA_{com}(i)(t)) * f\{abs[SigA_{com}(i)(t)], \tau(t)\}.$$

Here, f designates one of the modification functions of FIG. 8.

In the embodiment according to FIG. 8 e), the modification function is determined statistically. This is illustrated by means of FIG. 9 and FIG. 10.

Figure 9:
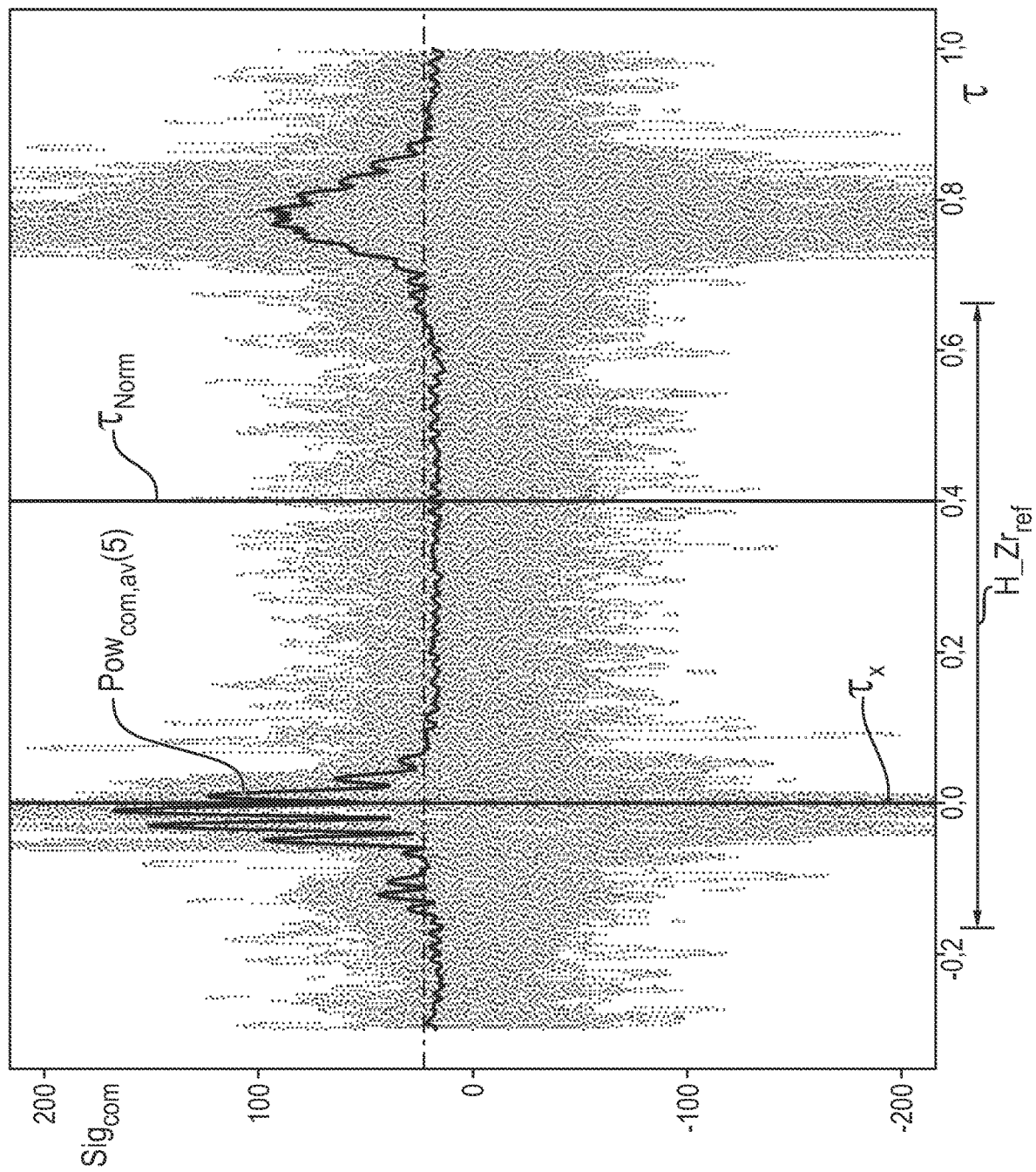
FIG. 9 is a view of a statistical determination of a modification function random sample.

FIG. 9 shows for level i=5 all the curves of the signal component $SigA_{com}(5)(x)$ of the compensation signal $Sig_{com}$, which were measured in the initialization phase, as well as the average curve $Pow_{com,av}(5)$, wherein the curves are mapped to the reference heartbeat time period $H\_Zr_{ref}$. The reference time $\tau=0$ is again the R wave. A standard time $\tau_{Norm}$ is predefined in the reference heartbeat time period $H\_Zr_{ref}$, for example $\tau_{Norm}=0.4$. The cardiogenic component $Sig_{kar}$ of the sum signal $Sig_{Sum}$ and hence of the compensation signal $Sig_{com}$ is negligibly small at this standard time. The steps described below are carried out for each reference time $\tau_x$ of a set with a plurality of reference times in the reference heartbeat time period $H\_Zr_{ref}$, and the times of this set cover the reference heartbeat time period $H\_Zr_{ref}$. This yields, as a whole, a characteristic, for example, the characteristic shown in FIG. 8 e).

Figure 10C:
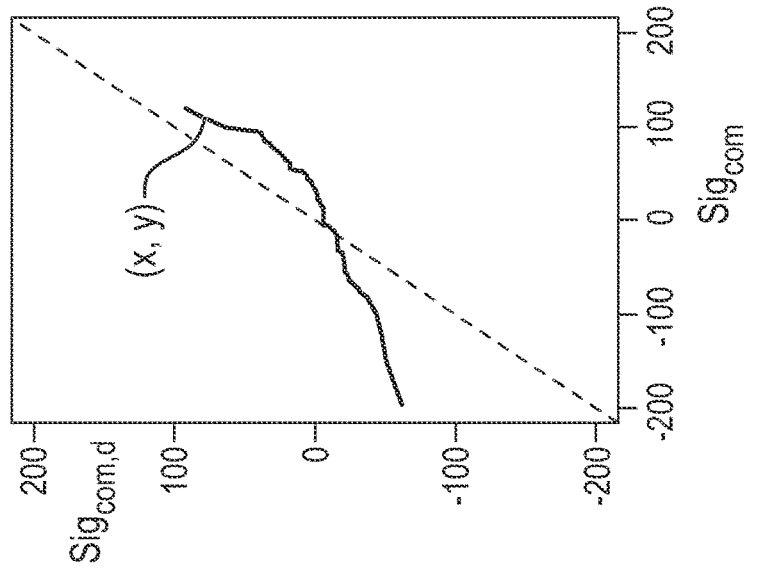
FIGS. 10a, 10b, 10c are a view of a statistical determination of a modification function: Distribution function, density function, characteristic.
Figure 10B:
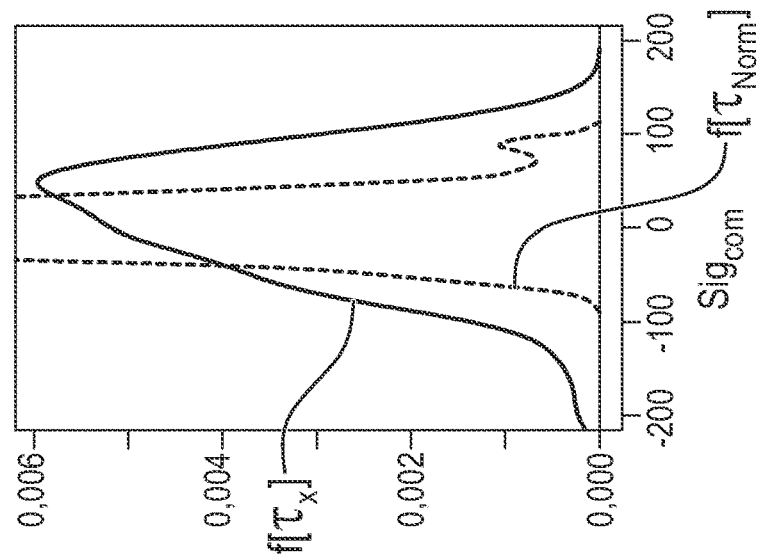
Figure 10A:
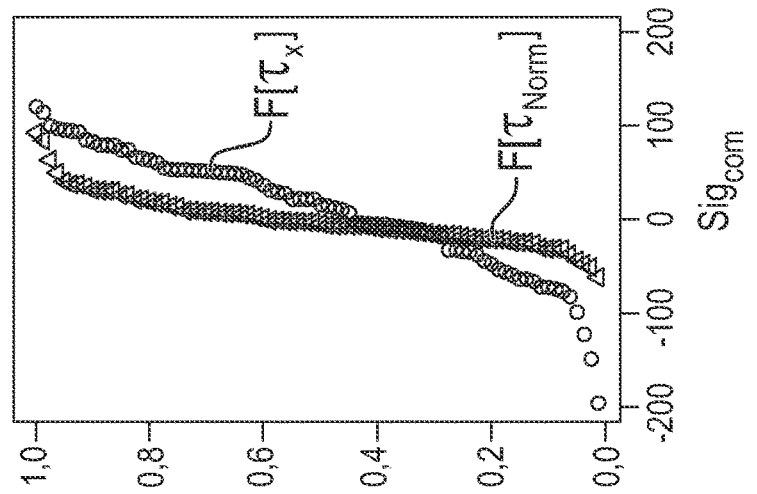

The values $SigA_{com}(t)(\tau_x)$ of the signal component $SigA_{com}(i)$ mapped to the reference heartbeat time period $H\_Zr_{ref}$, which values were measured for the reference time $\tau_x$, form a random sample. An empirical distribution function $F[\tau_x]$ is calculated by means of this random sample. The values that were measured for the standard time $\tau_{Norm}$ yield a standard random sample. An empirical standard distribution function $[\tau_{Norm}]$ is calculated by means of this standard random sample. FIG. 10 a) shows these two empirical distribution functions. An empirical density function $f[\tau_x]$ as well as an empirical standard density function $f[\tau_{Norm}]^{-1}$ can be calculated in the same manner by means of the two random samples. These are shown in FIG. 10 b). The density function is known to be the derivation of the distribution function. A value pair (x, y) with $x = Pow_{com,av}(5)(\tau_x)$ and $y = F[\tau_{Norm}]^{-1}\{F[\tau_x](\tau_x)\}$ is then calculated. $F[\tau_{Norm}]^{-1}$ is the inverse distribution function. This calculation is carried out for each time $\tau$ of the set and it yields a characteristic, which is shown as an example in FIG. 10 e).

The characteristic is used to map $SigA_{com}(i)(t)$ (x value of the characteristic) to $SigA_{com,d}(i)(t)$ (y value of the characteristic).

No assumption is made in one embodiment concerning the distribution. It is assumed in a variant that the two distribution functions $F[\tau_x]$ and $F[\tau_{Norm}]$ are distribution functions of a standard distribution. The two random samples are shifted to the respective mean value, so that the expected value of the normal distribution equals 0 and the two variances $\sigma[\tau_{Norm}]$ and $\sigma[\tau_x]$ are estimated empirically. Now, $y = \sigma[\tau_{Norm}]/\sigma[\tau_x] * x$.

FIG. 11 shows a view with contour lines for the derivation of a modification function. The relative time $\tau$ in the reference heartbeat time period $H\_Zr_{ref}$ is plotted again on the horizontal axis and an indicator of the muscle activity of the respiratory muscles is plotted on the vertical axis. This indicator of the muscle activity is preferably calculated, for example, as follows, on the basis of the compensation signal $Sig_{com}$: The compensation signal $Sig_{com}$ is rectified (the magnitude is formed from each signal value). The rectified signal is filtered by means of a low-pass filter, so that an enveloping curve signal is formed. Sections of this enveloping curve signal, which are not located at a characteristic heartbeat time and are therefore caused by the cardiac activity and not by the muscle activity of the respiratory muscles, are cut out by calculation. This procedure can also be called "gating." The gaps are filled by interpolation over the remaining ranges. The resulting enveloping curve signal Env is also related to the reference heartbeat time period $H\_Zr_{ref}$ and is used as an indicator of the muscle activity. It is also possible to use the compensation signal $Sig_{com}$ as an indicator of the muscle activity.

A part of the random sample obtained in the initialization phase, namely, the part that assumes this signal value $Env(\tau)$ or $Sig_{com}(\tau)$ at this reference time $\tau$, belongs to each reference time $\tau$ of the reference heartbeat time period $H\_Zr_{ref}$ and to each value for the muscle activity, i.e., e.g., for each value of the enveloping curve signal Env or for each value $Sig_{com}(\tau)$ of the compensation signal $Sig_{com}$. This random sample yields an empirical variance. Contour lines for different values of the empirical variance (dispersion) σ are entered, for example, for $\sigma=\sigma_1$, $\sigma=\sigma_2$, $\sigma=\sigma_4$ and $\sigma=\sigma_6$. Entered is a reference range Ref of the reference heartbeat time period $H\_Zr_{ref}$ in which the cardiogenic signal $Sig_{kar}$ is negligibly small.

The modification function is specified such that the following applies: The modification function maps the empirical variance for a determined signal value of the muscle activity and for a determined reference time $\tau_x$ to an empirical variance for the same signal value and for a reference time $\tau_x$ in the reference range Ref. This is shown as an example in FIG. 11 for the two values $Mus_1$ and $Mus_2$ of the indicator of the muscle activity (shown on the vertical axis), for the empirical variances $\sigma=\sigma_3$ and $\sigma=\sigma_7$ and for the two reference times $\tau_1$ and $\tau_2$, which are located in the reference heartbeat time period $H\_Zr_{ref}$ and outside the reference range Ref. The value $[\tau_1, Mus_1]$ is mapped to the value $[\tau_{Norm}, Mus_1]$, and the value $[\tau_2, Mus_2]$ to the value $[\tau_{Norm}, Mus_2]$.

The principle of FIG. 11 generalizes the principle $y=\sigma[\tau_{Norm}]/\sigma[\tau_x]*x$, which was explained with reference to FIG. 10. According to FIG. 11

$$y=[\tau_{Norm}, Mus_x]/\sigma[\tau_x, Mus_x]*x.$$

FIG. 12 shows a variant, which makes do without an initialization phase. A typical curve of the cardiogenic signal $Sig_{kar}$ in the reference heartbeat time period $H\_Zr_{ref}$ is shown in the top part of FIG. 12, and a predefined curve for $\alpha_x=\alpha_x(\tau)$ is shown in the bottom part. The higher the performance, i.e., the magnitude of the signal value $Sig_{kar}(\tau)$, the lower is the value $\alpha_x(\tau)$. This predefined curve is stored in the memory 9. Other modification instructions may be used in this variant as well.

In another variant, the current effective value (RMS) of the sum signal $Sig_{Sum}$, which varies over time, is additionally included in the reference modification signal section Mod(i). The respiratory signal $Sig_{res}$ can be separated even better from the cardiogenic signal $Sig_{kar}$ in case of great fluctuations in the muscle activity of the respiratory muscles. The variant that was explained with reference to FIG. 11 is an example of how the effective value is taken into consideration.

Figure 17:
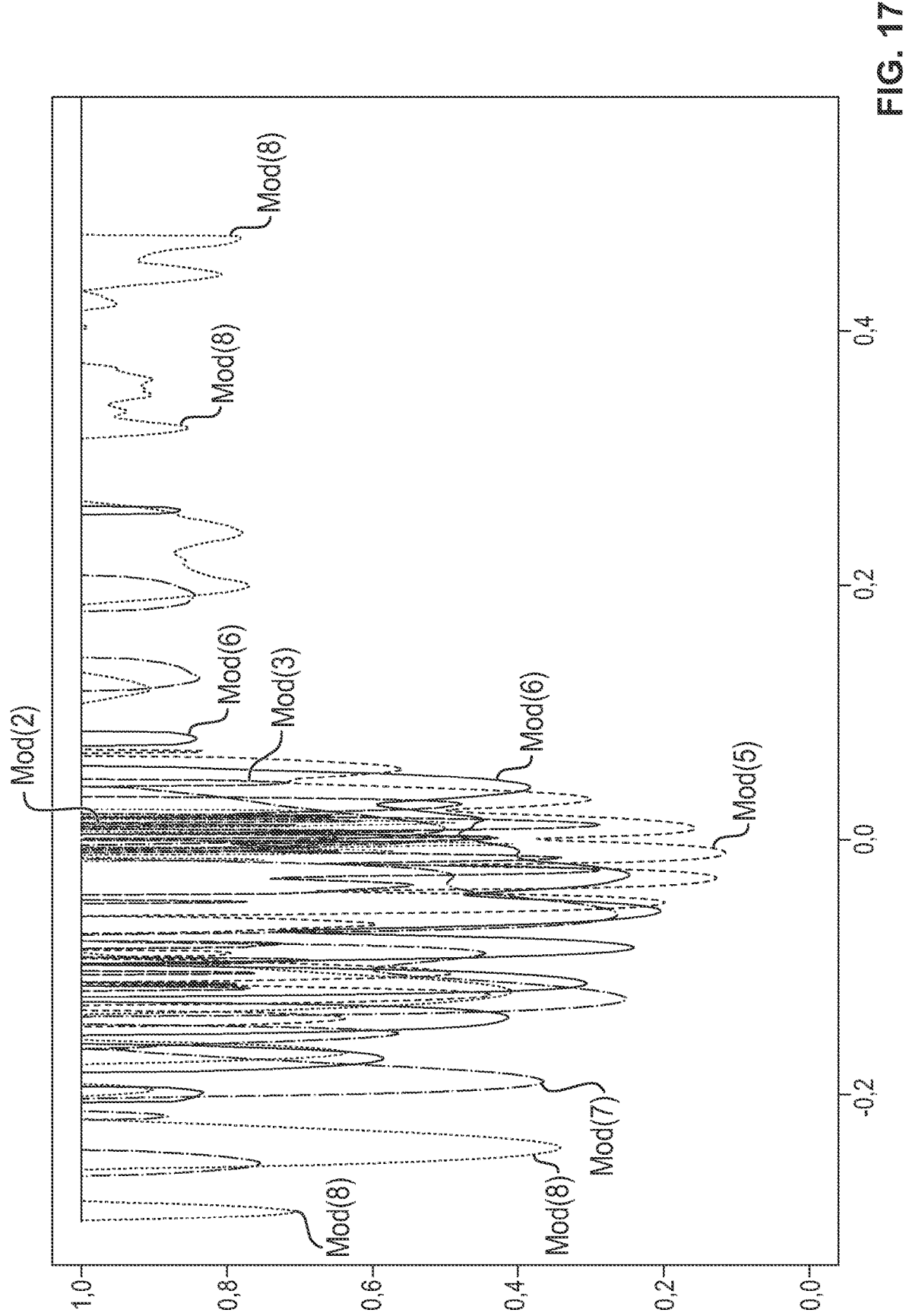
FIG. 17 is a view of the n reference modification signal sections Mod(1), Mod(n) for the n levels.

FIG. 17 shows as an example the n reference modification signal sections Mod(1), . . . , Mod(n) for the n levels.

Figure 18:
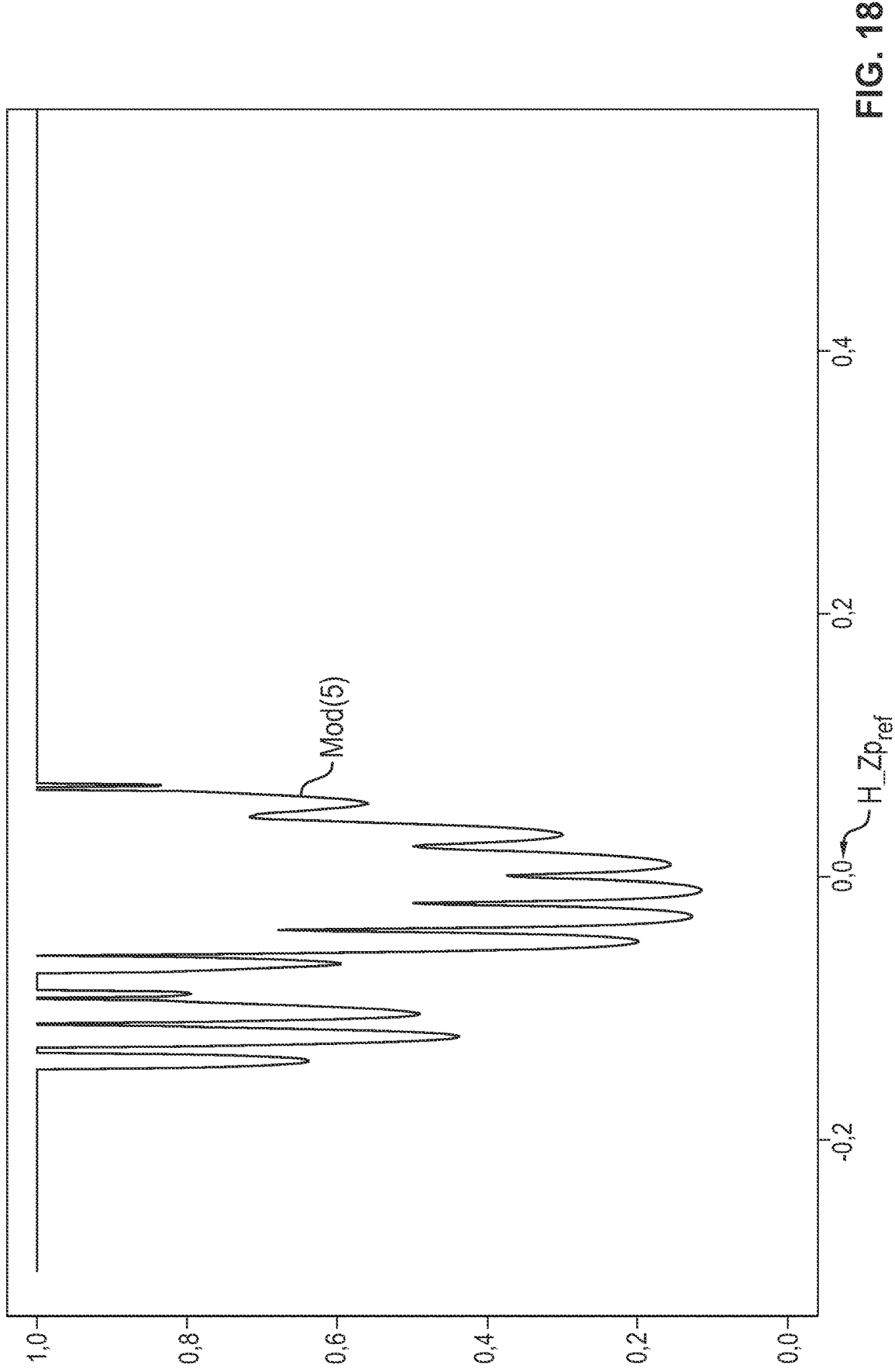
FIG. 18 is a view of the reference modification signal section Mod(5) for level No. 5.

FIG. 18 shows the curve of the reference modification signal section Mod(5) for level No. 5.

The steps just described for generating the n reference modification signal sections Mod(1), . . . , Mod(n) in the initialization phase and for updating them in the subsequent use phase are preferably carried out with the low scanning frequency. The n reference modification signal sections Mod(1), . . . , Mod(n) are preferably stored in the memory 9.

As was described above, the compensation function block 20 from FIG. 6 and FIG. 7 yields with the high scanning frequency a respective new value $Sig_{com}(t)$ for the compensation signal $Sig_{com}$. The attenuation function block 21 yields a respective new value $Sig_{res,est}(t)$ for the estimated respiratory signal $Sig_{res,est}$ with this high scanning frequency and also with the low scanning frequency. The attenuation function block 21 now carries out the following steps:

The functional unit 22 decomposes a section of the compensation signal $Sig_{com}$, which covers the latest K scanning times of the high scanning frequency, into n signal component sections for n frequency bands (levels), for example, by a wavelet transformation. These sections are are hereinafter designated by $SigA_{com}(1), \ldots, SigA_{com}(n)$.

The following steps are carried out for each level i (i=1, . . . , n) in the use phase:

The functional unit 24 positions the reference modification signal section Mod(i) with the correct time relative to the heartbeat. The functional unit 24 uses for this the beginning or the exact time $H\_Zp(x)$ of the heartbeat x, which the functional units 12 and 13 have detected.

If a reference modification signal section Mod(i) does not fully cover a signal component section $SigA_{com}(i)$, it is filled up in a suitable manner, preferably with the constant value 1 or by interpolation. If the reference modification signal section Mod(i) is too long, it is preferably cut off in a projecting range in a suitable manner.

The reference modification signals section Mod(i) positioned with correct time is applied by the functional unit 26 to the signal component section $SigA_{com}(i)$ for level No. i in order to generate the attenuation signal component section $SigA_{com,d}(i)$, for example, by multiplication:

$$SigA_{com,d}(i)(t)=Mod(i)[\tau(t)]*SigA_{com}(i)(t)$$

or by one of the alternatives shown in FIG. 8 *b*) through FIG. 8 *e*).

A section $SigA_{com,d}(i)$ of the attenuation compensation signal component $SigA_{com,d}(i)$, which in turn covers the latest K scanning times, is generated hereby.

The functional unit 25 generates from the n sections $SigA_{com,d}(1), \ldots, SigA_{com,d}(n)$ of the n attenuated compensation signal components $Sig_{com,d}(1), \ldots, Sig_{com,d}(n)$ by back transformation a section $SigA_{com}$ of the attenuated compensation signal, which is used as the newest section of the respiratory signal $Sig_{res,est}$ to be estimated and which covers K scanning times.

In the embodiment just described, the value of a reference modification signal Mod(i) of a level i depends only on the relative time τ (or on the cardiac phase 1) in the reference heartbeat time period $H\_Zr_{ref}$. Consequently, the same reference modification signal section Mod(i) is used for each heartbeat. In one variant, the reference modification signal section Mod(i) is adapted in the use phase in each heartbeat depending on the value of the anthropological parameter measured during that heartbeat, such as this is also carried out for the cardiogenic reference signal section $SigA_{kar,ref}$, e.g., depending on the filling level of the lungs or on an indicator of the current posture of the patient P. A learning method is preferably applied in the initialization phase in order to automatically learn the dependence of the reference modification signal section Mod(i) on the anthropological parameter or each anthropological parameter.

In a variant, a respiratory reference modification signal section $Mod_{res}(i)$, which describes the time curve of an attenuation during a breath, is generated during the initialization phase in addition to the reference modification signal section Mod(i), which depends on the cardiac phase $\Phi$. $\text{Mod}_{res}(i)[\text{T}_{res}]$ is likewise a number between 0 and 1 for each relative breath time $\text{T}_{res}$. The attenuation signal component section $\text{SigA}_{com,d}(i)$ is calculated, e.g., according to the instruction $\text{SigA}_{com,d}(i)(t) = \{\text{Mod}(i)[\tau(t)]^* \text{Mod}_{res}(i)[\tau_{res}(t)]\}^{1/2} * \text{SigA}_{com}(i)(t).$ In a variant, the current muscle exertion $MA=MA(t)$ is estimated instead of the breath time $\text{T}_{res}$. The respiratory reference modification signal section $\text{Mod}_{res}(i)$ depends on this muscle exertion MA, i.e., $\text{Mod}_{res}(i) = \text{Mod}_{res}(i)(MA)$. The attenuation signal component section $\text{SigA}_{com,d}(i)$ is calculated in this variant, e.g., according to the instruction $\text{SigA}_{com,d}(i)(t) = \{\text{Mod}(i)[\tau(t)]^* \text{Mod}_{res}(i)[MA(t)]\} * \text{SigA}_{com}(i)(t).$ In one embodiment, the signal values of the estimated respiratory signal $\text{Sig}_{res,est}$ are outputted with a time delay, which results from the calculation time, which the attenuation function block 21 needs for the just listed calculation steps. Below, $\Delta t$ designates the distance between two consecutive scanning times at the high scanning frequency, and the number K is such that the attenuation function block 21 manages the calculation steps during the time period $K^*\Delta t$. The attenuation function block 21 carries out the calculation steps listed above for a respective section of the compensation signal $\text{Sig}_{com}$, which section covers the latest K scanning times. The resulting K signal values for the estimated respiratory signal $\text{Sig}_{res,est}$ are outputted one after another. The attenuation function block 21 processes again a section with the most recent K signal values of the compensation signal $\text{Sig}_{com}$ overlapping in time with the output.

Both function blocks 20 and 21 preferably create a fast signal path for the steps that were carried out with the high scanning frequency and a slow signal path for the steps that are carried out with the low scanning frequency. The two signal paths are arranged in parallel to one another. A device and a process for processing physiological signals by means of a fast signal path and of a slow signal path are described, for example, in DE 10 2011 016 804 A1 incorporated by reference, and in EP 2845616 B1 incorporated by reference.

Figure 19:
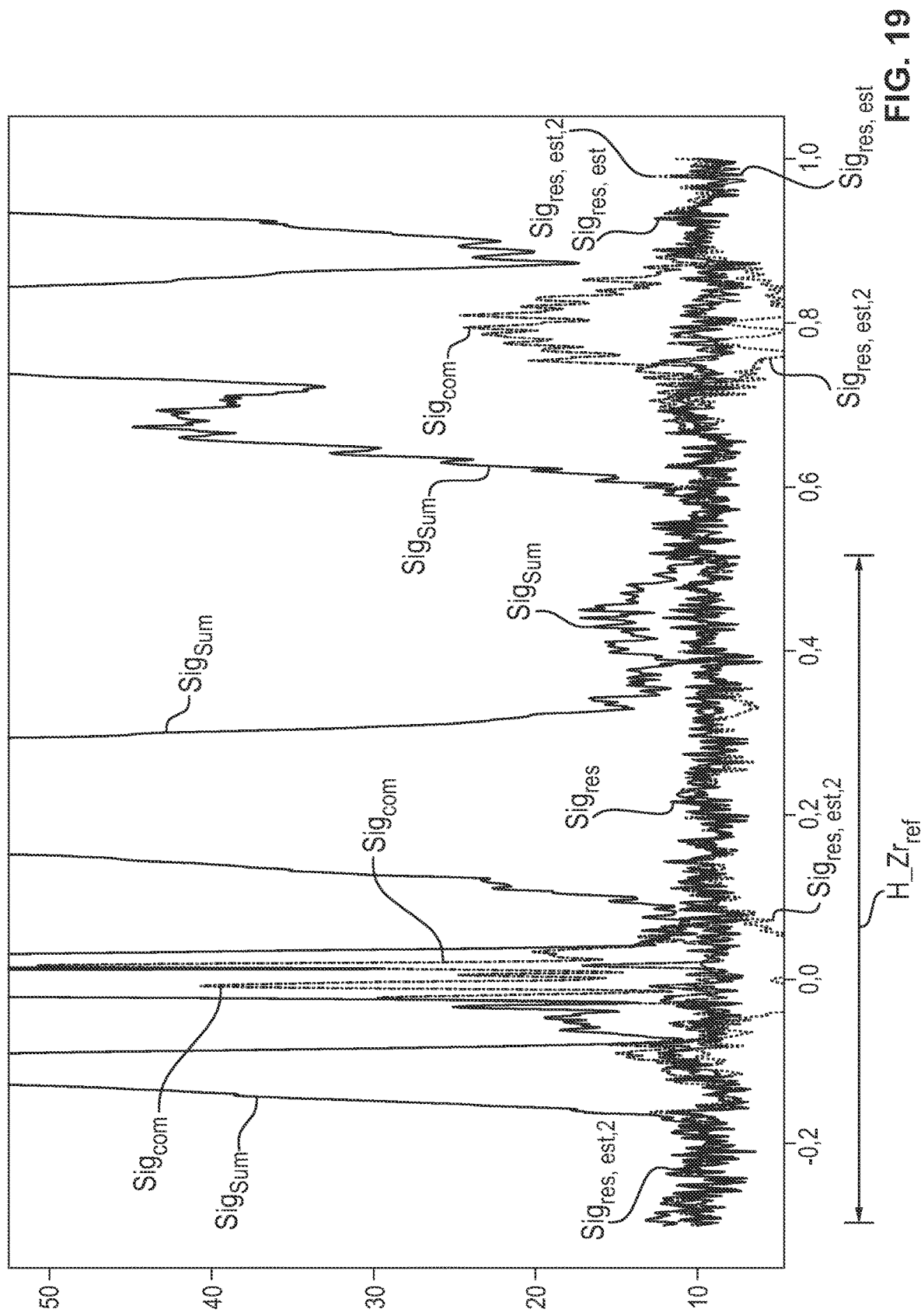
FIG. 19 is a view of in a superimposed view the respective time curve of the respective effective values of the following signals: Actual respiratory signal $Sig_{res}$, the sum signal $Sig_{Sum}$ as well as three determined signals, which estimate the respiratory signal $Sig_{res}$.
Figure 20:
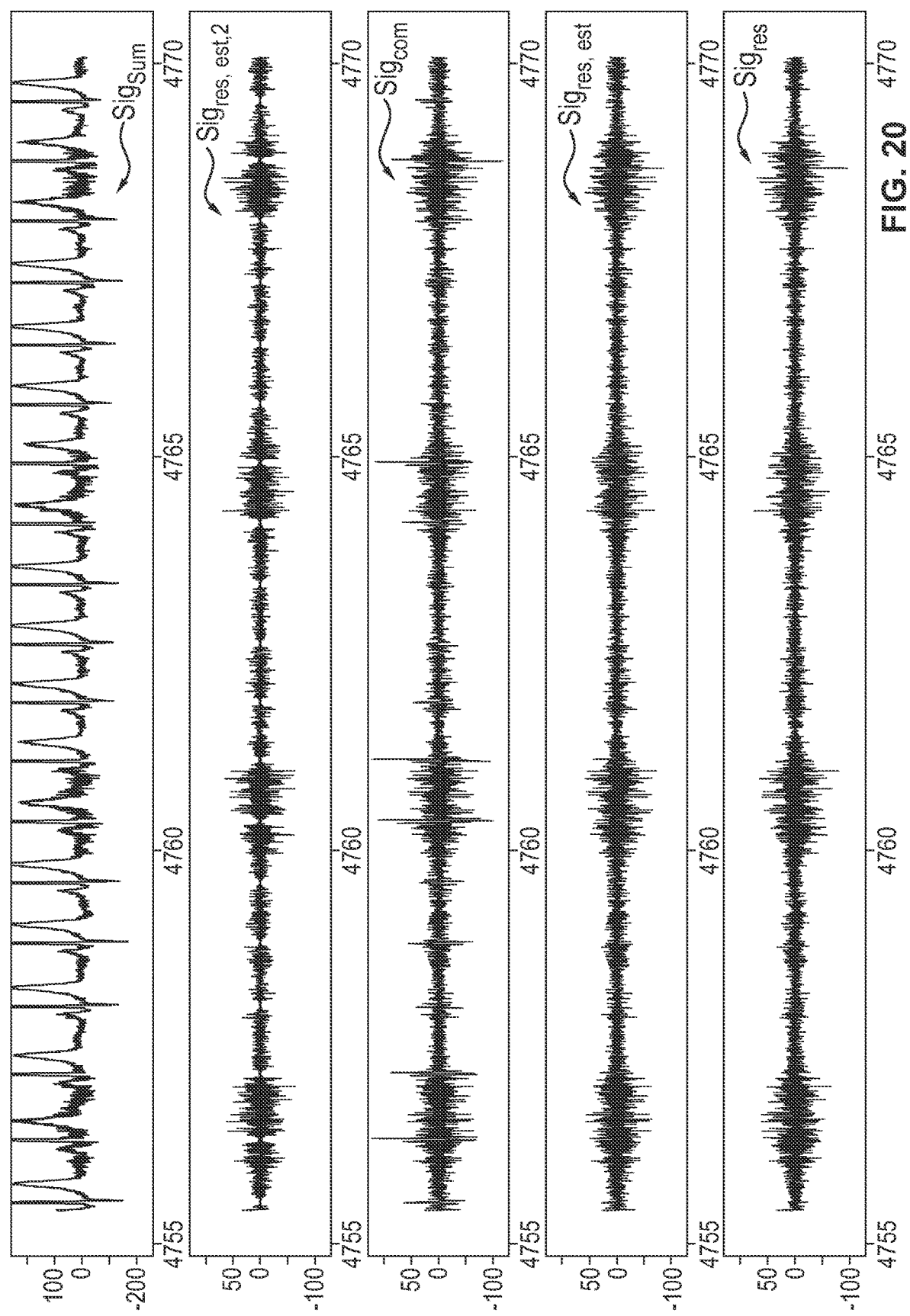
FIG. 20 is a view of the five effective value curves of FIG. 19 in five separate views.

In a preferred embodiment possible values for the interpretation parameters of the process are compared to one another in advance, the comparison being carried out by means of so-called residual performance analysis. FIG. 19 and FIG. 20 show as an example five signals, which describe the respective resulting time curve of the effective value (RMS), doing so in a superimposed view (FIG. 19) and in five separate views (FIG. 20). To generate this view, sections of the five signals, which cover 19 heartbeats, were superimposed to one another (R wave at t=0.0). The residual performance analysis is preferably carried out on the basis of at least 60 heartbeats. The effective value does not ideally vary or it does so only little over the time. The effective value curves pertain to the following signals here:

$\text{Sig}_{Sum}$ is the sum signal, which is obtained by a signal processing of the measured values from the measuring electrodes 2.1.1 through 2.2.2 and is an input signal for the compensation function block 20, $\text{Sig}_{com}$ is the compensation signal, which has been generated by the compensation function block 20, wherein the synthetic cardiogenic signal $\text{Sig}_{kar,syn}$ was subtracted from the sum signal $\text{Sig}_{Sum}$, $\text{Sig}_{res}$ is the actual respiratory signal, $\text{Sig}_{res,est}$ is the estimate generated by the two function blocks 20 and 21 for the actual respiratory signal $\text{Sig}_{res}$, $\text{Sig}_{res,est,2}$ is an estimate for the respiratory signal $\text{Sig}_{res}$, which is determined from the sum signal $\text{Sig}_{Sum}$ by using only the attenuation function block 21, but not the compensation function block 20, cf. FIG. 13.

The compensation signal $\text{Sig}_{com}$, which the compensation function block 20 has generated, still has a high effective value in the QRS phase from −0.1 sec to +0.1 sec. The estimated respiratory signal $\text{Sig}_{res,est,2}$, which was generated without the use of the compensation function block 20, was attenuated too greatly during the QRS phase. The estimate $\text{Sig}_{res,est}$ generated according to the present invention comes very close to the actual respiratory signal $\text{Sig}_{res}$.

Figure 21:
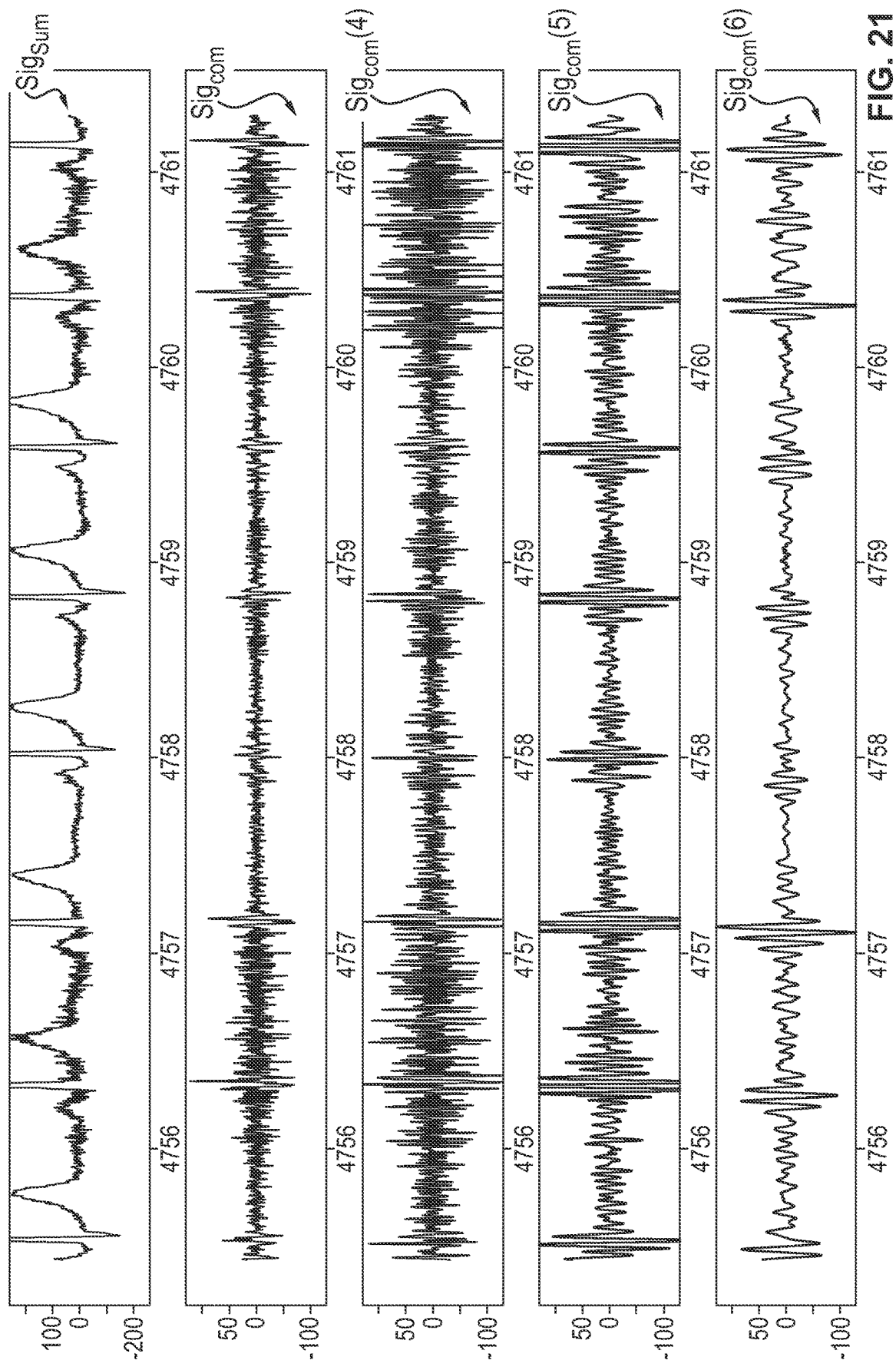
FIG. 21 is a view of the sum signal $Sig_{Sum}$, the compensation signal $Sig_{com}$ and three signal components $Sig_{com}(4)$, $Sig_{com}(5)$, $Sig_{com}(6)$ for the three levels 4, 5, 6.

FIG. 21 shows the sum signal $\text{Sig}_{Sum}$, the compensation signal $\text{Sig}_{com}$ and the three signal components $\text{Sig}_{com}(4)$, $\text{Sig}_{com}(5)$ and $\text{Sig}_{com}(6)$ for the three levels 4, 5 and 6.

A preferred embodiment of the present invention can be applied, for example, if the ventilator 1 shall be regulated on the basis of the respiratory signal $\text{Sig}_{res,est}$ determined according to the present invention. The steps of the compensation function block 20 assume that the heartbeat time $H\_Zp(x)$ of a heartbeat is detected sufficiently accurately, cf. FIG. 4, FIG. 6 and FIG. 7. It is only then that the cardiogenic reference signal section $\text{SigA}_{kar,ref}$ for this heartbeat can be positioned correctly with correct time in the synthetic cardiogenic signal $\text{Sig}_{kar,syn}$. However, the heartbeat time $H\_Zp(x)$ can be detected with sufficient accuracy only during the QRS phase. According to the preferred embodiment only the attenuation function block 21 is used therefore at first, i.e., the embodiment according to FIG. 13 is carried out, until the heartbeat time $H\_Zp(x)$ is detected with sufficiency accuracy during the QRS phase. As soon as the heartbeat time $H\_Zp(x)$ is detected, the compensation function block 20 additionally updates the compensation signal $\text{Sig}_{com}$ until the heartbeat time period $H\_Zr(x)$ has passed.

In one variant, the time of the current heartbeat is estimated until the QRS phase is reached and the heartbeat time $H\_Zp(x)$ can be detected with sufficient accuracy. For example, a prediction is carried out on the basis of the previous heartbeats and preferably of an estimated heartbeat frequency in order to estimate the current heartbeat time $H\_Zp(x)$.

While specific embodiments of the invention have been shown and described in detail to illustrate the application of the principles of the invention, it will be understood that the invention may be embodied otherwise without departing from such principles.

| List of Reference Numbers | |
| --- | --- |
| 1 | Ventilator; it mechanically ventilates and/or monitors the patient P; it comprises the signal processing unit 5 and the display unit 18 |
| 2.1.1, 2.1.2 | First set of measuring electrodes on the skin of the patient P; it yields measured values for the electrical sum signal $\text{Sig}_{Sum}$ |
| 2.2.1, 2.2.2 | Second set of measuring electrodes on the skin of the patient; it yields additional measured values for the sum signal $\text{Sig}_{Sum}$ |

-continued

| List of Reference Numbers | |
|---|---|
| 3 | Pneumatic sensor in front of the mouth of the patient P; it measures the volume flow Vol' and the airway pressure $P_{aw}$; it comprises the transducer 3.1 and the pressure sensor 3.2 |
| 3.1 | Transducer of sensor 3; it taps air from the fluid connection between the lungs Lu of the patient P and the ventilator 1 |
| 3.2 | Pressure sensor proper of sensor 3 |
| 4 | Optical sensor with an imaging device and with an image processing unit; it measures the geometry of the body of patient P, from which the current filling level of the lungs Vol is derived by calculation |
| 5 | Signal processing unit; it comprises the function blocks 20 and 21, carries out the steps of the process according to the present invention, has read access and write access to the memory 9 |
| 6 | Probe in the esophagus Sp; it measures the pneumatic pressure $P_{es}$ in the esophagus Sp; connected to catheter 7 |
| 7 | Catheter in the esophagus Sp of patient P |
| 8 | Flexible connection piece in the mouth of patient P; connected to the catheter 7 |
| 9 | Memory, to which the signal processing unit 5 has read access and write access and in which the cardiogenic reference signal section $SigA_{kar,\,ref}$ and the respiratory reference modification signal sections $Mod_{res}(i)$ are stored |
| 10 | Functional unit of the compensation function block 20: It generates the synthetic cardiogenic signal $Sig_{kar,\,syn}$ |
| 11 | Functional unit of the compensation function block 20: It compensates the influence of the cardiogenic signal $Sig_{kar}$ on the sum signal $Sig_{Sum}$, for example, by the subtraction of $Sig_{kar,\,syn}$, with the use of the synthetic cardiogenic signal $Sig_{kar,\,syn}$ |
| 12 | Functional unit of the signal processing unit 5: It detects in the sum signal $Sig_{Sum}$ the respective QRS time period of each heartbeat |
| 13 | Functional unit of the signal processing unit 5: It detects the exact heartbeat time $H\_Zp(n)$ of each heartbeat |
| 14 | Functional unit of compensation function block 20: It superimposes the sum signal sections for each heartbeat by calculation |
| 15 | Functional unit of compensation function block 20: It generates a cardiogenic reference signal section $SigA_{kar,\,ref}$ |
| 16 | Functional unit of the compensation function block 20: It positions the cardiogenic reference signal sections $SigA_{kar,\,ref}$ as a function of the heartbeat time $H\_Zp(x)$ with the correct time; it composes the positioned cardiogenic reference signal sections $SigA_{kar,\,ref}$ into the synthetic cardiogenic signal $Sig_{kar,\,syn}$ |
| 17 | Sensor at the ventilator 1; it measures the volume flow Vol' |
| 18 | Display unit of ventilator 1 |
| 20 | Compensation function block: It generates the synthetic cardiogenic signal $Sig_{kar,\,syn}$ and the compensation signal $Sig_{com}$ |
| 21 | Attenuation function block: It generates the estimated respiratory signal $Sig_{res,\,est}$ from, the compensation signal $Sig_{com}$ by attenuation |
| 22 | Functional unit of the attenuation function block 21: It decomposes the compensation signal $Sig_{com}$ into n signal components (frequency bands) |
| 23 | Functional unit of attenuation function block 21: It generates the estimated respiratory signal $Sig_{res,\,est}$ from the compensation signal $Sig_{com}$ by attenuation |
| 23(i) | Functional unit of the attenuation function block 21: It generates the attenuation signal component section $SigA_{com,\,d}(i)$ for the signal component (frequency band) i (i = 1, ..., n) from the signal component section $SigA_{com}(i)$ |
| 24 | Functional unit of attenuation function block 21: It generates the reference modification signal section $Mod(i)$ for the signal component (frequency band) i (i = 1, ..., n) |
| 25 | Functional unit of attenuation function block 21: It composes the attenuation signal component sections $SigA_{com,\,d}(1), \ldots, SigA_{com,\,d}(n)$ for the n signal components (frequency bands) by back transformation into the newest section $SigA_{com,\,d}$ of the attenuated compensated signal $SigA_{com,\,d}$, wherein this section is used as the most recent section of the estimated respiratory signal $Sig_{res,\,est}$ |
| 26 | Functional unit in the functional unit 23/23(i): It applies the reference modification signal $Mod(i)$ to the signal component $SigA_{com}(i)$ and generates the attenuation signal component $SigA_{com,\,d}(i)$ for the signal component (frequency band) i = 1, ..., n) |
| 27 | Gastric probe in the stomach Ma of patient P; it measures the gastric pressure $P_{ga}$ |
| 30 | Functional unit of attenuation function block 21: It generates the compensation signal sections from the compensation signal $Sig_{com}$ with the use of the characteristic heartbeat times |
| 31 | Functional unit: It generates the sought estimated respiratory signal $Sig_{res,\,est}$; uses the attenuation signal component sections $SigA_{com,\,d}(x), \ldots$ |
| 32 | Optional functional unit: It delays the sum signal $Sig_{Sum}$ for the run time, which is necessary for the determination of the characteristic heartbeat time $H\_Zp(x)$ |
| 37 | Optional gastric probe in the form of a measuring balloon in the stomach Ma, connected to catheter 7 |

-continued

| List of Reference Numbers | |
|---|---|
| Avg(i) | Mean signal value for the signal component (frequency band, level) No. i (i = 1, . . . , n), calculated from the average performance signal section $Pow_{com, av}(i)$ (i = 1, . . . , n) |
| Atm(1), . . . , Atm(4) | Time periods of breaths |
| Env | Resulting enveloping curve signal, preferably generated by "gating" |
| $F[\tau_{Norm}]$ | Empirical density function for the standard time $\tau_{Norm}$ |
| $F[\tau_x]$ | Empirical density function for the relative time $\tau_x$ |
| $F[\tau_{Norm}]$ | Empirical distribution function for the standard time $\tau_{Norm}$ |
| $F[\tau_x]$ | Empirical distribution function for the relative time $\tau_x$ |
| H_Zp(x) | Characteristic heartbeat time of the heartbeat x, detected by functional unit 13 |
| $H\_Zp_{ref}$ | Reference heartbeat time |
| H_Zr(x) | Heartbeat time period of the heartbeat x |
| $H\_Zr_{ref}$ | Reference heartbeat time period, covered by the cardiogenic reference signal section $SigA_{kar, ref}$ and by the reference modification signal section Mod(i) |
| Lu | Lungs of patient P |
| M | Number of heartbeats, which are used to generate the reference modification signal section Mod(i) (i = 1, . . . , n) |
| Ma | Stomach of patient P; it accommodates the gastric probe 37 |
| Mod(i) | Reference modification signal section for level No. i; it covers the reference heartbeat time period $H\_Zr_{ref}$ |
| $Mod_{res}(i)$ | Respiratory reference modification signal section for level No. i; it covers the reference heartbeat time period $H\_Zr_{ref}$ |
| $Mus_1\ Mus_2$ | Values that the indicator of the muscle activity assumes |
| n | Number of signal components (levels), into which the functional unit 22 decomposes the compensation signal $Sig_{com}$ |
| N | Number of heartbeats, which are used to generate the cardiogenic reference signal section $SigA_{kar, ref}$ |
| $P_{kar}$ | Pneumatic signal for the pressure in the ventricle |
| $Ph_{kar}$ | Acoustic signal for the volume of the heart sounds |
| $Pow_{com}(i)$ | Performance signal for level No. i (i = 1, . . . , n) |
| $Pow_{com, av}(i)$ | Average performance signal section for level No. i; it covers a reference heartbeat time period $H\_Zr_{ref}$ |
| Φ(i) | Threshold value for level i |
| $Sig_{com}$ | Compensation signal; it is generated by the compensation function block 20 by compensation of the contribution of the synthetic cardiogenic signal $Sig_{kar, syn}$ to the sum signal $Sig_{Sum}$ |
| $Sig_{com}(x)$ | Signal section of the compensation signal $Sig_{com}$ for heartbeat x |
| $Sig_{com}(i)$ | Signal component for level No. i (i = 1, . . . , n) |
| $Sig_{com, d}(i)$ | Attenuation signal component for level No. i (i = 1, . . . , n) |
| $SigA_{com}(i)(x)$ | Signal component section for level No. i (i = 1, . . . , n) of the compensation signal $Sig_{com}$ for heartbeat x, generated by functional unit 22 by decomposing the compensation signal $Sig_{com}$ |
| $SigA_{com, d}(i)(x)$ | Attenuation signal component section for level No. i (i = 1, . . . , n) for heartbeat x, generated by functional unit 23(i) with the use of the reference modification signal section Mod(i) from the signal component section $SigA_{com, d}(i)$ |
| $Sig_{kar}$ | Cardiogenic signal; it brings about the cardiac activity of patient P, estimated by the synthetic cardiogenic signal $Sig_{kar, syn}$ |
| $SigA_{kar, ref}$ | Cardiogenic reference signal section; it approximately describes the curve of the cardiogenic signal $Sig_{kar}$ during a single heartbeat; it pertains to the reference heartbeat time period $H\_Zr_{ref}$ |
| $SigA_{kar}(x)$ | Cardiogenic signal section for heartbeat x, generated from the cardiogenic reference signal section $SigA_{kar, ref}$ by using a value of an anthropological parameter measured during the heartbeat x |
| $Sig_{kar, syn}$ | Synthetic cardiogenic signal; it is an estimate for the cardiogenic signal $Sig_{kar}$; generated by functional unit 10 from the signal sections $SigA_{kar, syn}(x)$ |
| $SigA_{kar, syn}(x)$ | Section of the synthetic cardiogenic signal $Sig_{kar, syn}$ for heartbeat x |
| $Sig_{res}$ | Respiratory signal to be determined; it causes the intrinsic breathing activity of patient P |
| $Sig_{res, est}$ | Estimate determined according to the present invention for the respiratory signal $Sig_{res}$ to be determined |
| $Sig_{res, est, 2}$ | Estimate for the respiratory signal $Sig_{res}$ to be determined, which is determined from the sum signal $Sig_{Sum}$ by the sum signal $Sig_{Sum}$ being directly present as an input signal at the attenuation function block 21 |
| $Sig_{Sum}$ | Electrical sum signal, generated by signal processing unit 5 with the use of measured values of the measuring electrodes 2.1.1 through 2.2.2 or other sensors; it is formed by a superimposition of the respiratory signal $Sig_{res}$ to the cardiogenic signal $Sig_{kar}$ |
| $SigA_{Sum}(x)$ | Section of the sum signal $Sig_{Sum}$ for heartbeat x in the heartbeat time period H_Zr(x) |
| φ(i) | Threshold value (threshold) for level No. i (i = 1, . . . , n), calculated with the use of the mean signal value Avg(i) |
| $T, \tau_x$ | Relative heartbeat time in the reference heartbeat time period $H\_Zr_{ref}$ |
| $T_{Norm}$ | Standard time in the reference heartbeat time period $H\_Zr_{ref}$ at which the cardiac activity is negligibly low |

| List of Reference Numbers | |
|---|---|
| τ(t) | Relative heartbeat time in the reference heartbeat time period τ, which corresponds to the absolute time t in a heartbeat time period H_Zr(x) |

What is claimed is:

1. A process for determining an estimate for a respiratory signal, wherein the respiratory signal is correlated with an intrinsic breathing activity and/or with a mechanical ventilation of a patient, the process comprising the steps of:
predefining a reference heartbeat time period;
providing a data-processing signal processing unit, wherein the signal processing unit performs the steps of:
receiving measured values of at least one sum signal sensor, the at least one sum signal sensor being configured to measure a signal generated in the body of the patient;
generating a sum signal with the use of the measured values, the sum signal comprising a superimposition of the respiratory signal to be estimated and of a cardiogenic signal correlated with cardiac activity of the patient;
detecting a plurality of heartbeats with use of the sum signal;
detecting a respective heartbeat time period, in which the heartbeat takes place for each detected heartbeat with the use of the sum signal;
one of calculating an intermediate signal from the sum signal, the intermediate signal being configured to compensate an influence of the cardiac activity on the sum signal, or using the sum signal as the intermediate signal;
one of calculating at least one attenuation signal or determining the attenuation signal by a read access to a memory, wherein the attenuation signal or each attenuation signal correlates with an average time curve of a contribution of the cardiogenic signal onto the intermediate signal in the reference heartbeat time period;
generating for at least one detected heartbeat, a respective intermediate signal section as a section of the intermediate signal, which is located in the heartbeat time period of the one heartbeat;
determining for each scanning time in the heartbeat time period of the one heartbeat a reference time in the reference heartbeat time period, which corresponds to the scanning time and determine a respective value of the attenuation signal or each attenuation signal at the reference time;
generating an attenuated intermediate signal section for the heartbeat time period from the intermediate signal section with the use of the attenuation signal values thus determined, the attenuated intermediate signal section is calculated to correlate with the curve of the respiratory signal in the heartbeat time period; and
generating the estimate for the respiratory signal with the use of the attenuated intermediate signal section;
one of monitoring the patient based of the estimate for the respiratory signal, regulating a ventilator based on the estimate for the respiratory signal, and displaying the estimate for the respiratory signal.

2. A process in accordance with claim 1, wherein:
when a heartbeat-free time period occurs between two consecutive heartbeat time periods, the signal processing unit performs the steps of:
calculating a non-attenuated intermediate signal section by using of the intermediate signal for at least one heartbeat-free time period; and
composing the attenuated intermediate signal sections for the estimate of the respiratory signal.

3. A process in accordance with claim 2, further comprising:
composing the non-attenuated intermediate signal sections for the estimate of the respiratory signal.

4. A process in accordance with claim 1, wherein the signal processing unit performs the steps of:
automatically calculating the attenuation signal and storing it in the memory;
wherein during the calculation, the signal processing unit performs the steps of:
generating a signal section random sample, which comprises the respective intermediate signal section for several detected heartbeats of the plurality of heartbeats;
computationally mapping each intermediate signal section of the signal section random sample to the reference heartbeat time period; and
wherein the calculating of the attenuation signal is performed with the use of the mapped intermediate signal sections of the signal section random sample.

5. A process in accordance with claim 4, wherein:
the step of calculating the attenuation signal with the use of the mapped intermediate signal sections comprises steps in which the signal processing unit:
calculates an electrical power indicator random sample with a plurality of progress over time curves of an indicator of an electrical power in the reference heartbeat time period;
wherein the signal processing unit calculates a respective progress over time curve of the electrical power indicator of a plurality of mapped intermediate signal sections of the signal section random sample;
calculates an average progress over time curve for the electrical power indicator in the reference heartbeat time period by a statistical averaging over the progress over time curves of the electrical power indicator random sample; and
using the average progress over time curve in the calculating of the attenuation signal.

6. A process in accordance with claim 5, wherein the signal processing unit performs the steps of:
calculating an electrical power average value for the electrical power in the course of the reference heartbeat time period with the use of the electrical power indicator random sample;
further calculating the attenuation signal with the use of the average progress over time curve and with the use of the electrical power average value.

7. A process in accordance with claim 6, wherein:
the signal processing unit calculates the attenuation signal with the use of a quotient of the electrical power average value and the average progress over time curve.

8. A process in accordance with claim 4, wherein:
a standard reference time of the reference heartbeat time period is predefined, at which the cardiogenic signal is negligibly low compared to the respiratory signal;
the step of calculating the attenuation signal with the use of the mapped intermediate signal sections comprises steps in which the signal processing unit:
generates for at least one reference time of the reference heartbeat time period a respective signal value random sample; wherein
each signal value random sample comprises values of the mapped intermediate signal sections of the signal section random sample;
calculates an empirical distribution function for the at least one reference time with the use of the signal value random sample;
generates a standard signal value random sample, wherein the standard signal value random sample comprises values at the standard reference time of the mapped intermediate signal sections of the signal section random sample;
calculates an empirical standard distribution function for the standard reference time with the use of the standard signal value random sample; and
further calculates the attenuation signal with the use of the empirical distribution function or each empirical distribution function as well as of the standard distribution function.

9. A process in accordance with claim 1, wherein:
a plurality of frequency bands are predefined; and
the signal processing unit further comprises the steps of:
calculating at least one respective attenuation signal for each predefined frequency band, the attenuation signal being configured as an indicator of the average progress over time curve of the contribution of the cardiogenic signal to the intermediate signal in the reference heartbeat time period which contribution occurs in this frequency band;
for at least one detected heartbeat and each frequency band, the signal processing unit generating a respective component of the intermediate signal section, for the heartbeat time period of the one detected heartbeat, which signal section component occurs in the frequency band;
generating an attenuated intermediate signal section component for the one detected heartbeat with the use of the attenuation signal for the frequency band from the component of the intermediate signal section which attenuated intermediate signal section component occurs in the frequency band; and
generating the attenuated intermediate signal section for this at least one detected heartbeat with the use of the attenuated intermediate signal section components generated for the one detected heartbeat and for the predefined frequency bands.

10. A process in accordance claim 1, wherein:
the step of calculating the intermediate signal comprises individual steps in which the signal processing unit, with use of a plurality of detected heartbeat time periods and of the sum signal
generates a cardiogenic reference signal section and stores it in the memory, wherein the cardiogenic reference signal section describes an average progress over time curve of the cardiogenic signal in the course of the reference heartbeat time period;
the signal processing unit calculates a compensated signal as the intermediate signal, by the signal processing unit computationally compensating, for at least one detected heartbeat the influence of the cardiac activity during the one detected heartbeat on the sum signal with the use of the cardiogenic reference signal section stored in the memory and the use of the detected heartbeat time period of the one detected heartbeat.

11. A process in accordance with claim 10, wherein:
the step of compensating the influence of the cardiac activity on the sum signal by computationally compensation comprises the steps in which for at least one detected heartbeat, the signal processing unit performs the steps of:
measuring at least one parameter value, which a predefined anthropological parameter assumes during this heartbeat;
calculating an adapted signal section with the use of the cardiogenic reference signal section stored in the memory and use of the parameter value of the anthropological parameter or of at least one value of the anthropological parameter, which value was measured during this heartbeat;
compensating the influence of the cardiac activity on the sum signal by calculating with the use of the adapted signal section and the detected heartbeat time period.

12. A non-transitory computer readable medium comprising a computer program, which can be executed on a signal processing unit and causes the signal processing unit to carry out a process in accordance with claim 1 during an execution of the computer program on the signal processing unit when the signal processing unit receives measured values of at least one sum signal sensor, which measures a signal generated in the body of the patient.

13. A process in accordance claim 1, wherein:
the step of calculating the intermediate signal comprises individual steps in which the signal processing unit, with use of a plurality of detected heartbeat time periods and of the sum signal
generates a cardiogenic reference signal section and stores it in the memory, wherein the cardiogenic reference signal section describes an average progress over time curve of the cardiogenic signal in the course of the reference heartbeat time period;
the signal processing unit calculates a compensated signal as the intermediate signal, by the signal processing unit computationally compensating, for every detected heartbeat, the influence of the cardiac activity during every detected heartbeat on the sum signal with the use of the cardiogenic reference signal section stored in the memory and the use of the detected heartbeat time period of every detected heartbeat.

14. A process in accordance with claim 13, wherein:
the step of compensating the influence of the cardiac activity on the sum signal by computationally compensation comprises the steps in which for each detected heartbeat, the signal processing unit performs the steps of:
measuring a value, which a predefined anthropological parameter assumes during this heartbeat;
calculating an adapted signal section with the use of the cardiogenic reference signal section stored in the memory and use of the value of the anthropological parameter or of at least one value of the anthropological parameter, which value was measured during this heartbeat;

compensating the influence of the cardiac activity on the sum signal by calculation with the use of the adapted signal section and the detected heartbeat time period.

15. A signal processing unit having a read access at least temporarily a read access to a memory; and being configured to electrically determine an estimate for a respiratory signal, wherein the respiratory signal is correlated with an intrinsic breathing activity and/or a mechanical ventilation of a patient, wherein a computer-accessible description of a reference heartbeat time period is stored in the memory;

wherein the signal processing unit is configured to receive measured values from at least one sum signal sensor;

wherein the at least one sum signal sensor is configured to measure a signal generated in the body of the patient;

wherein the signal processing unit is configured to generate a sum signal with the use of such measured sum signal sensor values;

wherein the sum signal comprises a superimposition of:
of the respiratory signal to be estimated and
of a cardiogenic signal correlating with a cardiac activity of the patient, wherein the signal processing unit is configured to detect a plurality of heartbeats and
for each heartbeat of the detected plurality of heartbeats, a respective heartbeat time period in which this heartbeat takes place, wherein the signal processing unit is configured to:
calculate an intermediate signal by an approximate compensation by calculation of the influence of the cardiac activity on the sum signal or
use the sum signal as the intermediate signal, wherein the signal processing unit is configured to calculate at least one attenuation signal or to determine the at least one attenuation signal by a read access to the memory, where the attenuation signal correlates with an average progress over time curve of the contribution of the cardiogenic signal to the intermediate signal in the reference heartbeat time period, wherein the signal processing unit is configured to generate for at least one detected heartbeat, of the detected heartbeat plurality, a respective intermediate signal section as a section of the intermediate signal which is in the heartbeat time period of this heartbeat, wherein the signal processing unit is configured to determine, for at least one scanning time in the heartbeat time period of this heartbeat;
a reference time in the reference heartbeat time period which corresponds to this scanning time, and
the respective value of the attenuation signal at this reference time, wherein the signal processing unit is configured to generate an attenuated intermediate signal section for the heartbeat time period from the intermediate signal section with the use of the attenuation signal values thus determined, wherein the attenuated intermediate signal section correlates with the progress over time of the respiratory signal in the heartbeat time period, and wherein the signal processing unit is configured to generate the estimate for the respiratory signal with the use of the attenuated intermediate signal section or each attenuated intermediate signal section.

16. A ventilator for the mechanical ventilation of a patient, wherein the ventilator
comprises a signal processing unit in accordance with claim 15 and
is configured to mechanically ventilate the patient as a function of the determined estimate for the respiratory signal.

17. A process for one of operating a ventilator for breathing of a patient, and for detecting abnormalities in the breathing of a patient, the process comprising the steps of:
providing a sum signal sensor configured to measure a signal generated in the patient, the signal being a superimposition of a respiratory signal and of a cardiogenic signal of the patient, the cardiogenic signal being correlated with the cardiac activity of the patient, the respiratory signal being correlated with the intrinsic breathing activity and/or with the mechanical ventilation of a patient;
receiving measured values from said sum signal sensor;
generating a sum signal with said measured values;
detecting in the sum signal a plurality of heartbeats;
detecting a heartbeat time period in which a respective heartbeat takes place for each of the plurality of detected heartbeats;
calculating from the sum signal an intermediate signal, the intermediate signal being configured to compensate for an influence of the cardiac activity on the sum signal, or using the sum signal as the intermediate signal;
calculating an attenuation signal or determining the attenuation signal by a read access to a memory;
the attenuation signal is calculated to correlate with an average time curve of a contribution of the cardiogenic signal with the intermediate signal in the reference heartbeat time period;
generating for one detected heartbeat, a respective intermediate signal section as a section of the intermediate signal, which is located in the heartbeat time period of the one heartbeat;
determining for each scanning time in the heartbeat time period of the one heartbeat a reference time in the reference heartbeat time period, which corresponds to this scanning time;
determining a respective value of the attenuation signal at this reference time;
generating an attenuated intermediate signal section for the heartbeat time period from the intermediate signal section with use of the attenuation signal values thus determined, wherein the attenuated intermediate signal section is correlated with the curve of the respiratory signal in the heartbeat time period; and
generating an estimate for the respiratory signal with use of the attenuated intermediate signal section;
one of operating the ventilator for the breathing of a patient using the estimate for the respiratory signal, detecting abnormalities in the breathing of a patient using the estimate for the respiratory signal, and displaying the estimate for the respiratory signal.

* * * * *